United States Patent
Uruma et al.

(10) Patent No.: US 11,819,600 B2
(45) Date of Patent: Nov. 21, 2023

(54) WASTE LIQUID RECEPTACLE, WASTE LIQUID RESERVOIR AND WASTE LIQUID SUCTION SYSTEM

(71) Applicant: DAIKEN MEDICAL CO., LTD., Osaka (JP)

(72) Inventors: Masayuki Uruma, Osaka (JP); Takeshi Wada, Osaka (JP); Kouhei Kazuhara, Osaka (JP); Yoshiro Ohashi, Osaka (JP)

(73) Assignee: DAIKEN MEDICAL CO., LTD., Osaka (JP)

( * ) Notice: Subject to any disclaimer, the term of this patent is extended or adjusted under 35 U.S.C. 154(b) by 9 days.

(21) Appl. No.: 17/760,642

(22) PCT Filed: Sep. 15, 2020

(86) PCT No.: PCT/JP2020/034805
§ 371 (c)(1),
(2) Date: Mar. 15, 2022

(87) PCT Pub. No.: WO2021/054297
PCT Pub. Date: Mar. 25, 2021

(65) Prior Publication Data
US 2022/0331505 A1    Oct. 20, 2022

(30) Foreign Application Priority Data
Sep. 20, 2019    (JP) .................................. 2019-171753

(51) Int. Cl.
*A61M 1/00*    (2006.01)
(52) U.S. Cl.
CPC .............. *A61M 1/604* (2021.05); *A61M 1/80* (2021.05); *A61M 2202/04* (2013.01)

(58) Field of Classification Search
CPC .... A61M 1/604; A61M 1/80; A61M 2202/04; A61M 1/882; A61M 1/60; A61M 1/68; A61M 1/682; A61M 1/88
See application file for complete search history.

(56) References Cited

U.S. PATENT DOCUMENTS 5,156,823 A * 10/1992 Hori .......................... A61L 2/16
                                                        422/561
5,238,582 A *  8/1993 Hori ........................ A61L 11/00
                                                        604/416
(Continued)

FOREIGN PATENT DOCUMENTS

CA         2641918 A1 *  8/2007  .......... A61M 1/0001
CN      106659824 A  *  5/2017  ............... A61L 2/18
(Continued)

OTHER PUBLICATIONS

International Search Report dated Nov. 24, 2020 in International (PCT) Application No. PCT/JP2020/034805.

*Primary Examiner* — Susan S Su
*Assistant Examiner* — Ted Yang
(74) *Attorney, Agent, or Firm* — Wenderoth, Lind & Ponack, L.L.P.

(57) ABSTRACT

A waste liquid receptacle includes first and second cover members for covering first and second openings, respectively. The first cover member is made of a material that is configured to: (i) be plastically deformed upward by a first suction force in a state where a second negative pressure is generated in an upper space; and (ii) plastically deform downward by a depressing force against the first cover member downward in a state where an openable and closable lid is open and the second negative pressure is released. The second cover member is made of a material that is configured: (i) not to be plastically deformed by a second suction force in a state where a first negative pressure is (Continued)

generated in a waste liquid receipt space; and (ii) to be broken without being plastically deformed when a depressing force is applied to the first cover member.

16 Claims, 16 Drawing Sheets

(56) References Cited

U.S. PATENT DOCUMENTS

| | | | | |
|---|---|---|---|---|
| 5,391,351 A * | 2/1995 | Kaufman | ............... | A61M 1/604 600/573 |
| 5,543,042 A * | 8/1996 | Filan | ................. | B65D 81/3205 210/466 |
| 5,543,118 A * | 8/1996 | Kaufman | ............... | A61M 1/69 422/292 |
| 5,549,585 A * | 8/1996 | Maher | ................... | A61M 1/882 141/319 |
| 5,589,145 A * | 12/1996 | Kaufman | ............... | A61M 1/604 604/82 |
| 5,637,104 A * | 6/1997 | Ball | ........................ | A61M 1/60 604/905 |
| 6,056,730 A * | 5/2000 | Greter | ................... | A61M 1/784 604/319 |
| 6,152,902 A * | 11/2000 | Christian | ............... | A61M 1/604 604/320 |
| 8,100,874 B1 * | 1/2012 | Jordan | ................... | A61M 1/79 604/319 |
| 10,807,755 B2 * | 10/2020 | Mäkiranta | ............... | A61M 1/63 |
| 11,129,928 B2 * | 9/2021 | Korkeamäki | ......... | A61M 39/24 |
| 2002/0026160 A1 * | 2/2002 | Takahashi | ............. | A61M 1/782 604/319 |
| 2003/0004475 A1 * | 1/2003 | Takahashi | ............. | A61M 1/882 604/326 |
| 2005/0215961 A1 * | 9/2005 | Romano | ............... | A61M 1/604 604/322 |
| 2006/0217674 A1 * | 9/2006 | Romano | ................. | A61M 1/71 604/320 |
| 2007/0244451 A1 * | 10/2007 | Romano | ......... | G06Q 10/08355 604/319 |
| 2008/0061064 A1 * | 3/2008 | Michaels | ............... | A61M 1/882 220/495.06 |
| 2017/0304511 A1 * | 10/2017 | Harpham | ............... | A61M 1/734 |
| 2018/0272051 A1 * | 9/2018 | Smith | .................... | B01D 46/88 |
| 2019/0365960 A1 * | 12/2019 | Jardret | .................... | A61M 1/60 |

FOREIGN PATENT DOCUMENTS

| | | | | |
|---|---|---|---|---|
| JP | 2003-519460 | | 6/2003 | |
| JP | 3956056 B2 * | | 8/2007 | .......... A61M 1/0001 |
| JP | 2019-517285 | | 6/2019 | |
| WO | WO-0124846 A1 * | | 4/2001 | .......... A61M 1/0001 |

* cited by examiner

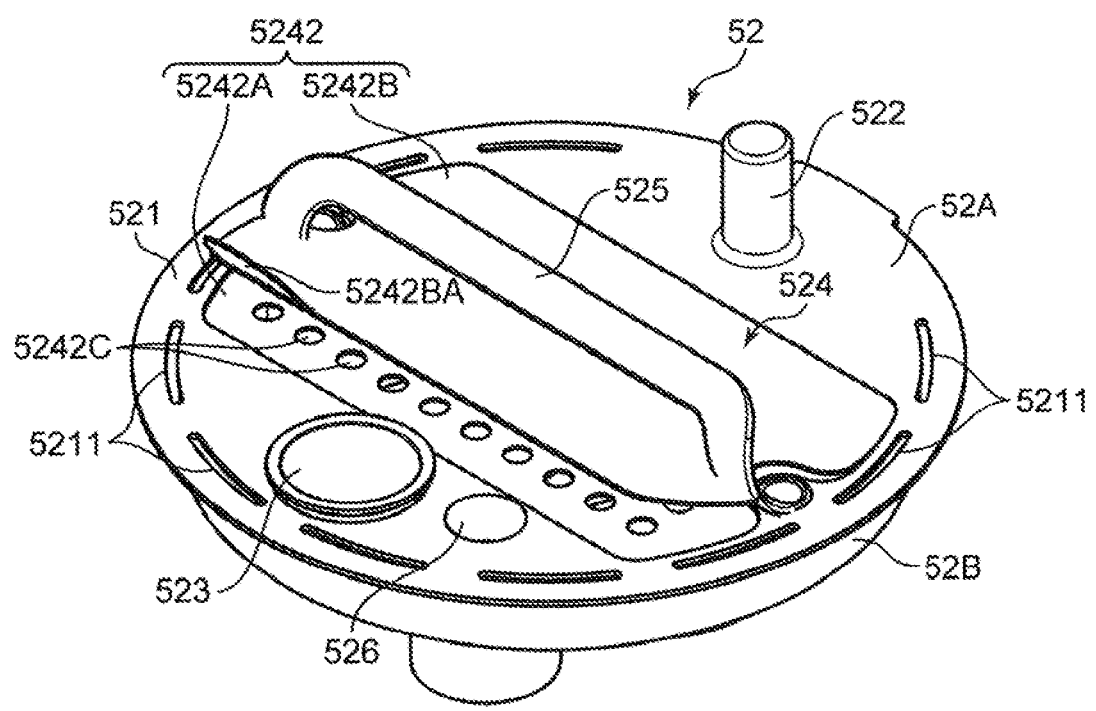

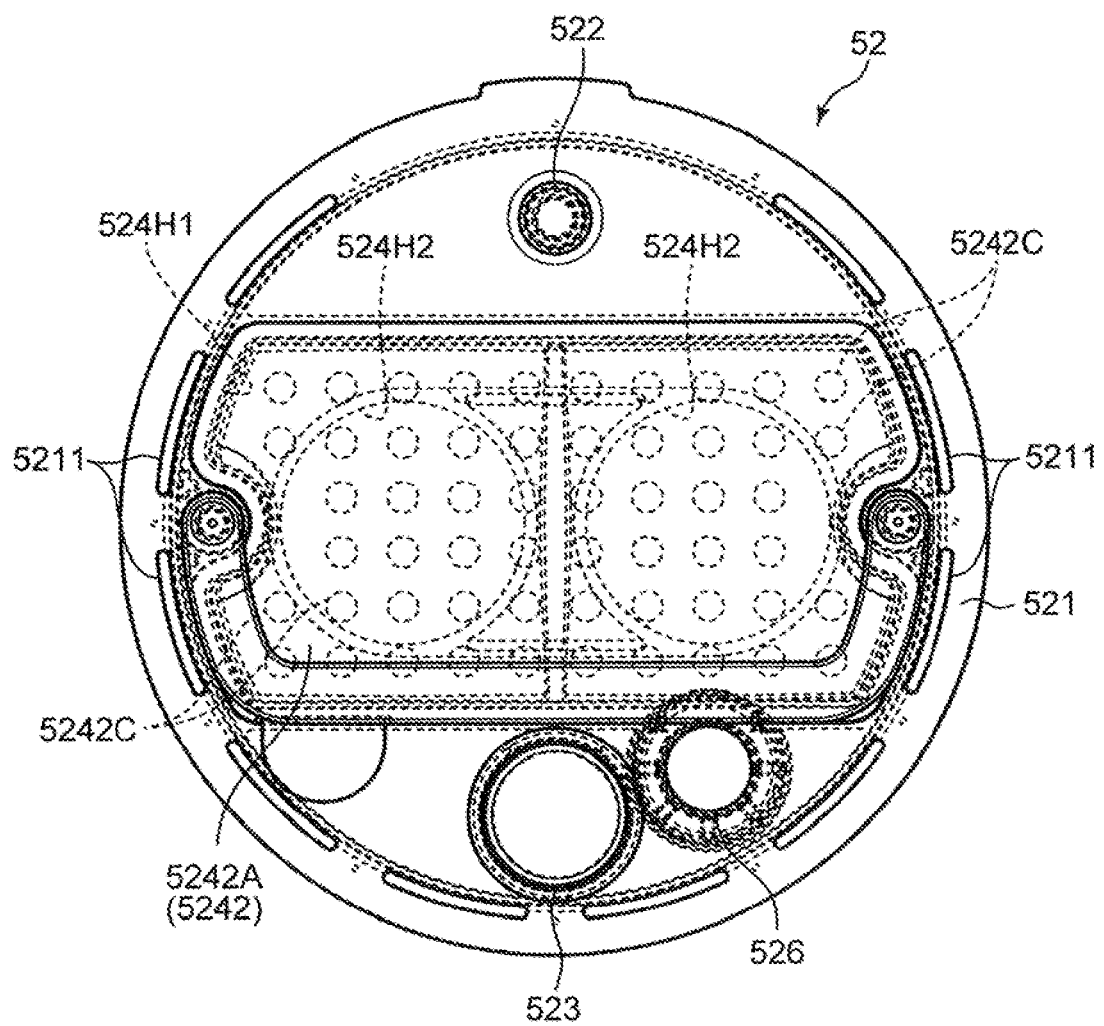

WASTE LIQUID RECEPTACLE, WASTE LIQUID RESERVOIR AND WASTE LIQUID SUCTION SYSTEM

TECHNICAL FIELD

The present invention relates to a waste liquid receiving receptacle that receives a predetermined waste liquid sucked by a suction force of a suction source, a waste liquid reservoir that includes the waste liquid receiving receptacle, and a waste liquid suction system.

BACKGROUND ART

There has been known a waste liquid suction system. In the waste liquid suction system, a waste liquid containing a body fluid of a patient or a cleaning liquid for cleaning a body cavity generated during surgery or the like is sucked by making use of a suction source disposed in a medical facility or the like, and the sucked waste liquid is reserved. The waste liquid suction system includes a waste liquid reservoir capable of reserving a waste liquid sucked by a suction force of the suction source. This type of waste liquid reservoir normally includes: a waste liquid receiving receptacle (liner) that receives a waste liquid; and a receptacle housing (canister) that houses the waste liquid receiving receptacle (see, for example, JP 2019-517285 A).

JP 2019-517285 A discloses a liner provided with a waste liquid treating agent storing portion that contains a waste liquid treating agent for treating a waste liquid. The waste liquid treating agent storing portion includes: a reservoir that is disposed in a lid of a liner and has an upper opening and a bottom opening; a flexible dome-shaped cap that covers an upper opening; and a perforated film seal that covers the bottom opening. In the waste liquid treating agent storing portion, when a depressing force that pushes the dome-shaped cap downward is applied to the dome-shaped cap, the perforated film seal is broken so that a waste liquid treating agent in the reservoir can be discharged into the liner.

In the liner disclosed in JP 2019-517285 A, in an operation to suck the waste liquid into the liner, a negative pressure is generated in an inner space of the liner by a suction force of a suction source. In the reservoir that stores a waste liquid treating agent, a perforated film seal is disposed on a bottom opening of the reservoir that opens facing the inner space of the liner, and the film seal has fine perforated pores. Accordingly, an inner space of the reservoir and the inner space of the liner communicate with each other through the fine perforated pores formed in the perforated film seal. In such a configuration, when a negative pressure is generated in the inner space of the liner, a negative pressure is generated also in the reservoir. When a negative pressure is generated in the reservoir, a suction force acts on the dome-shaped cap covering the upper opening of the reservoir. When the suction force acts on the dome-shaped cap, the dome-shaped cap is deformed downward as in the case where a downward depressing force is applied to the dome-shaped cap. Accordingly, there is a concern that, during the suction of the waste liquid into the liner, the perforated film seal is broken depending on the downward deformation of the dome-shaped cap so that a waste liquid treating agent in the reservoir is discharged into the liner.

SUMMARY OF INVENTION

The present invention has been made in view of such circumstances, and it is an object of the present invention to provide a waste liquid receiving receptacle including a waste liquid treating agent storing portion, in which the waste liquid receiving receptacle is capable of preventing a waste liquid treating agent from being discharged from the waste liquid treating agent storing portion during sucking a waste liquid, a waste liquid reservoir including such a waste liquid receiving receptacle, and a waste liquid suction system.

According to an aspect of the present invention, there is provided a waste liquid receiving receptacle housed in a receptacle housing. The receptacle housing includes a bottomed container-shaped housing body having an upper opening that opens upward, and an opening and closing lid supported by the housing body so as to be capable of opening and closing the upper opening, the waste liquid receiving receptacle being capable of receiving a predetermined waste liquid. The waste liquid receiving receptacle includes: a cylindrical body disposed in the housing body and having an opening on an upper side of the cylindrical body; a receptacle lid joined to an upper end of the cylindrical body, defining an upper space between the receptacle lid and the opening and closing lid on an upper side of the cylindrical body, and defining a waste liquid receiving space that receives a waste liquid sucked by a negative pressure generated in the waste liquid receiving space by communicating with the upper space in cooperation with the cylindrical body on a lower side of the upper space; and a waste liquid treating agent storing portion disposed on the receptacle lid, the waste liquid treating agent storing portion configured to store a waste liquid treating agent for treating a waste liquid received in the waste liquid receiving space. The waste liquid treating agent storing portion includes: a storing body having a first opening opened to face the upper space and a second opening opened to face the waste liquid receiving space, the storing body defining a treating agent storing space for storing the waste liquid treating agent between the first opening and the second opening; a first covering member joined to the storing body so as to cover the first opening; and a second covering member jointed to the storing body so as to cover the second opening. The first covering member is made of a material that plastically deforms upward by a suction force in a state where a negative pressure is generated in the upper space, and plastically deforms downward by a depressing force that pushes the first covering member downward in a state where the opening and closing lid is opened and the negative pressure in the upper space is released. The second covering member is made of a material that is not plastically deformed by a suction force in a state where a negative pressure is generated in the waste liquid receiving space and is broken without being plastically deformed in a case where the depressing force is applied to the first covering member.

According to another aspect of the present invention, there is provided a waste liquid reservoir including:
   a receptacle housing including: a bottomed container-shaped housing body having an upper opening that opens upward; and an opening and closing lid supported by the housing body so as to be capable of opening and closing the upper opening; and the above-mentioned waste liquid receiving receptacle housed in the receptacle housing and being capable of receiving a predetermined waste liquid.

A waste liquid suction system according to still another aspect of the present invention is a system configured to suck a predetermined waste liquid and to reserve the sucked waste liquid. The waste liquid suction system includes: a suction source; a suction path portion forming a suction path from a suction starting point portion serving as a suction starting point in sucking the waste liquid to the suction source; and the above-mentioned waste liquid reservoir disposed between the suction starting point portion and the suction source on the suction path, the waste liquid reservoir configured to reserve the waste liquid sucked from the suction starting point portion due to a suction force of the suction source.

According to the present invention, it is possible to provide a waste liquid receiving receptacle including a waste liquid treating agent storing portion, in which the waste liquid receiving receptacle is capable of preventing a waste liquid treating agent from being discharged from the waste liquid treating agent storing portion during sucking a waste liquid, a waste liquid reservoir including such a waste liquid receiving receptacle, and a waste liquid suction system.

Objects, technical features, and advantageous effects of the present invention will become more apparent with reference to the Detailed Description made hereinafter and the attached drawings.

BRIEF DESCRIPTION OF DRAWINGS

FIG. 15 is a perspective view of the first covering member illustrated in FIG. 14 in a state where an upper layer film is peeled off.

FIG. 16 is a plan view of the first covering member illustrated in FIG. 14 in a state where an upper layer film is peeled off.

DESCRIPTION OF EMBODIMENTS

Hereinafter, a waste liquid suction system and a waste liquid reservoir according to an embodiment of the present invention will be described with reference to drawings.

[Overall Configuration of Waste Liquid Suction System]

Figure 1:
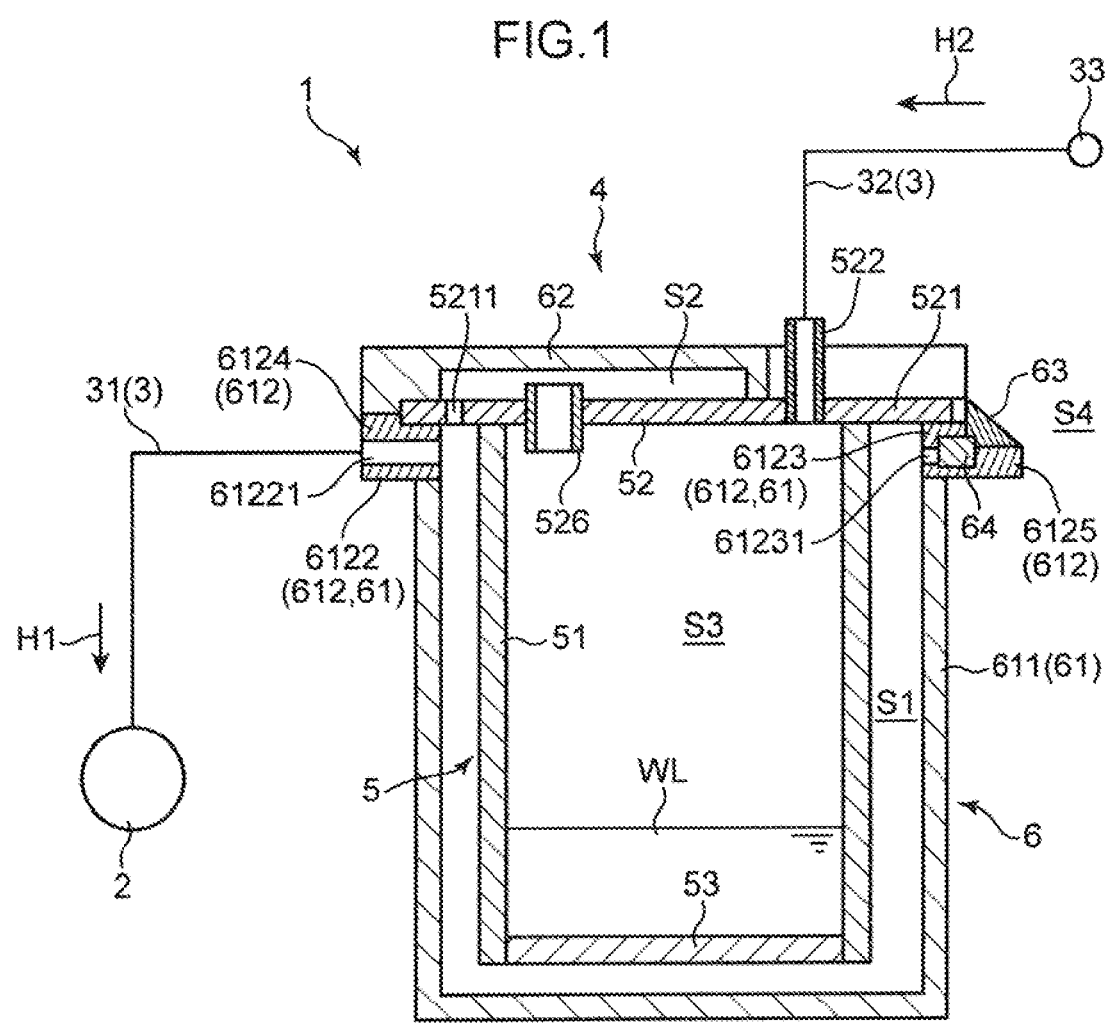
FIG. 1 is a view schematically illustrating a configuration of a waste liquid suction system to which a waste liquid reservoir including a liner according to an embodiment of the present invention is applied.

FIG. 1 is a view schematically illustrating the configuration of a waste liquid suction system 1 to which a waste liquid reservoir 4 including a liner 5 according to an embodiment of the present invention is applied. The waste liquid suction system 1 is a system where a waste liquid WL is sucked by a suction force of a predetermined suction source 2 and the sucked waste liquid WL is reserved. Specifically, the waste liquid suction system 1 is configured as follows. A waste liquid WL including a body fluid (blood and the like) of a patient and a cleaning liquid (physiological saline, for example) for cleaning a body cavity generated during surgery or the like is sucked by making use of a suction source 2 disposed in a medical facility or the like, and the sucked waste liquid WL is reserved. The waste liquid suction system 1 includes the suction source 2, a suction path portion 3, and a waste liquid reservoir 4.

The suction source 2 is disposed in a medical facility or the like. The structure of the suction source 2 is not particularly limited. However, the suction source 2 is formed of a suction pump or the like, for example.

The suction path portion 3 forms a suction path ranging from a suction starting point portion 33 that serves as a suction start point to the suction source 2 in sucking the waste liquid WL. The suction path portion 3 includes a first path member 31 and a second path member 32. The first path member 31 defines a first suction path between the suction source 2 and the waste liquid reservoir 4. The second path member 32 defines a second suction path between the waste liquid reservoir 4 and the suction starting point portion 33. The first path member 31 and the second path member 32 are respectively formed of a tube having flexibility, for example.

The waste liquid reservoir 4 is disposed between the suction starting point portion 33 and the suction source 2 on the suction path defined by the suction path portion 3. Both path members consisting of the first path member 31 and the second path member 32 are connected to the waste liquid reservoir 4. The waste liquid reservoir 4 is configured to reserve the waste liquid WL sucked from the suction starting point portion 33 by a suction force of the suction source 2.

[Configuration of Waste Liquid Reservoir]

Figure 2:
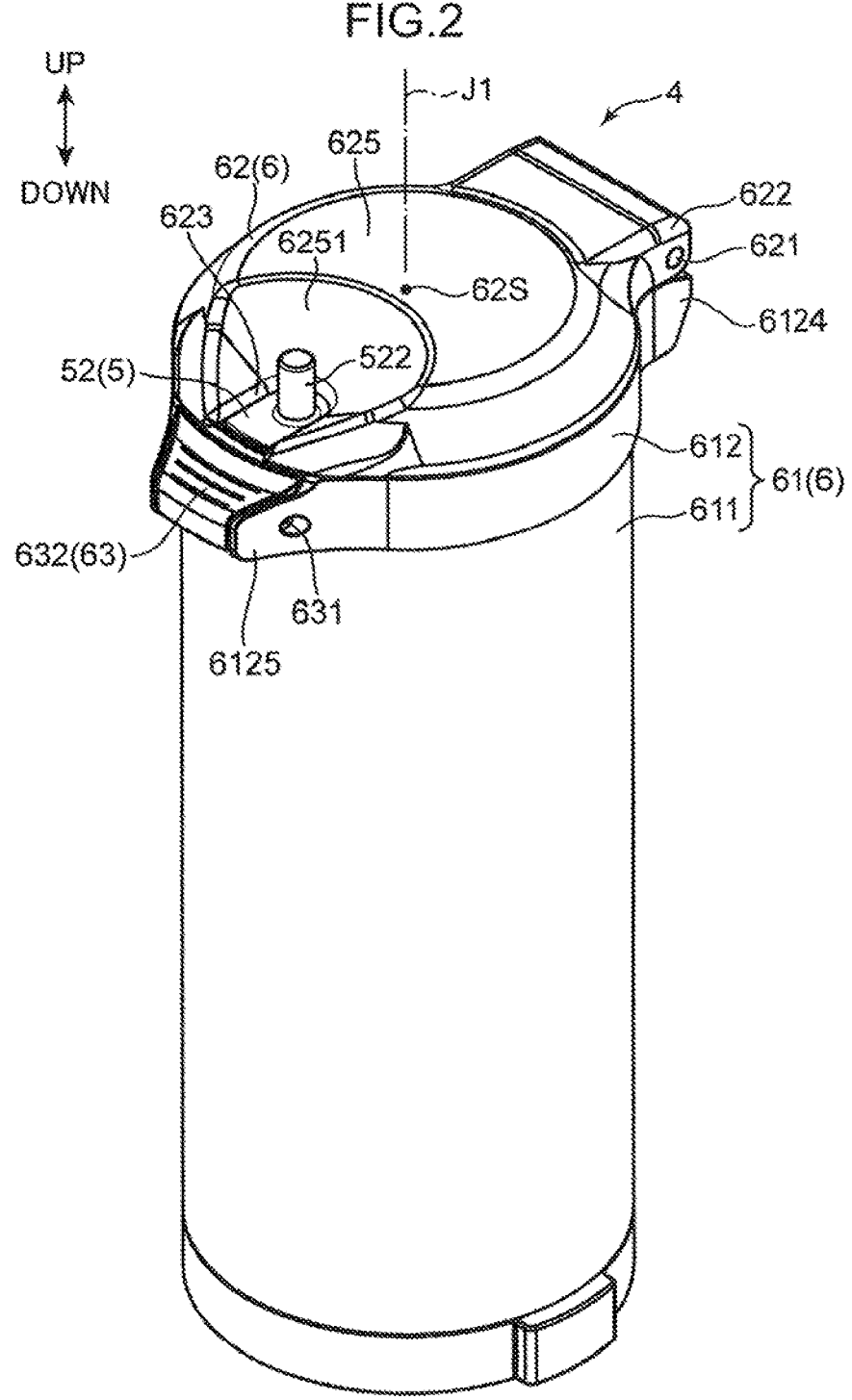
FIG. 2 is a perspective view illustrating the waste liquid reservoir.
Figure 3:
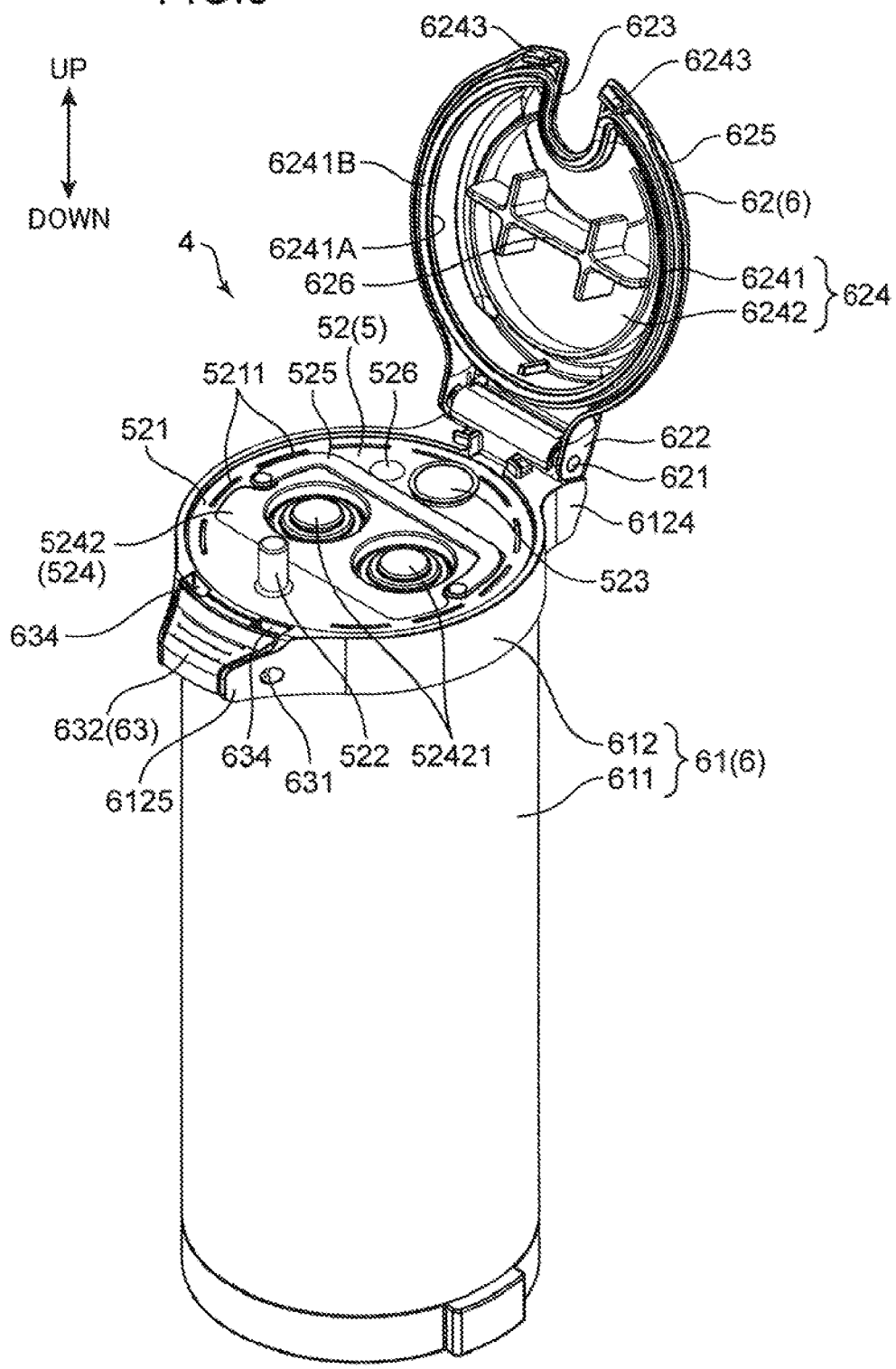
FIG. 3 is a perspective view of the waste liquid reservoir illustrating a state where an opening and closing lid of a canister is disposed at an open position.
Figure 4:
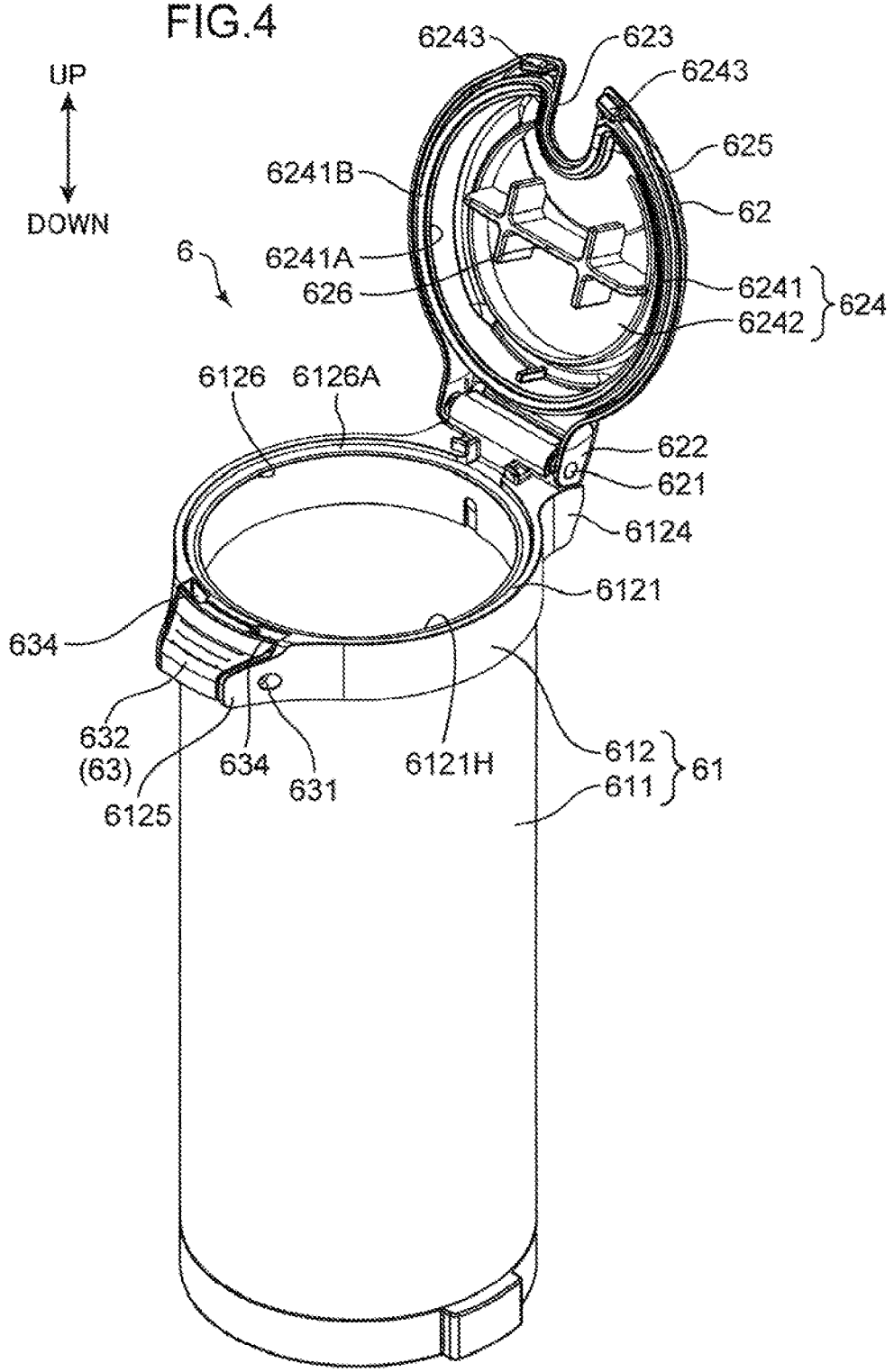
FIG. 4 is a perspective view of the waste liquid reservoir illustrating a state where a liner is removed from the canister.
Figure 5:
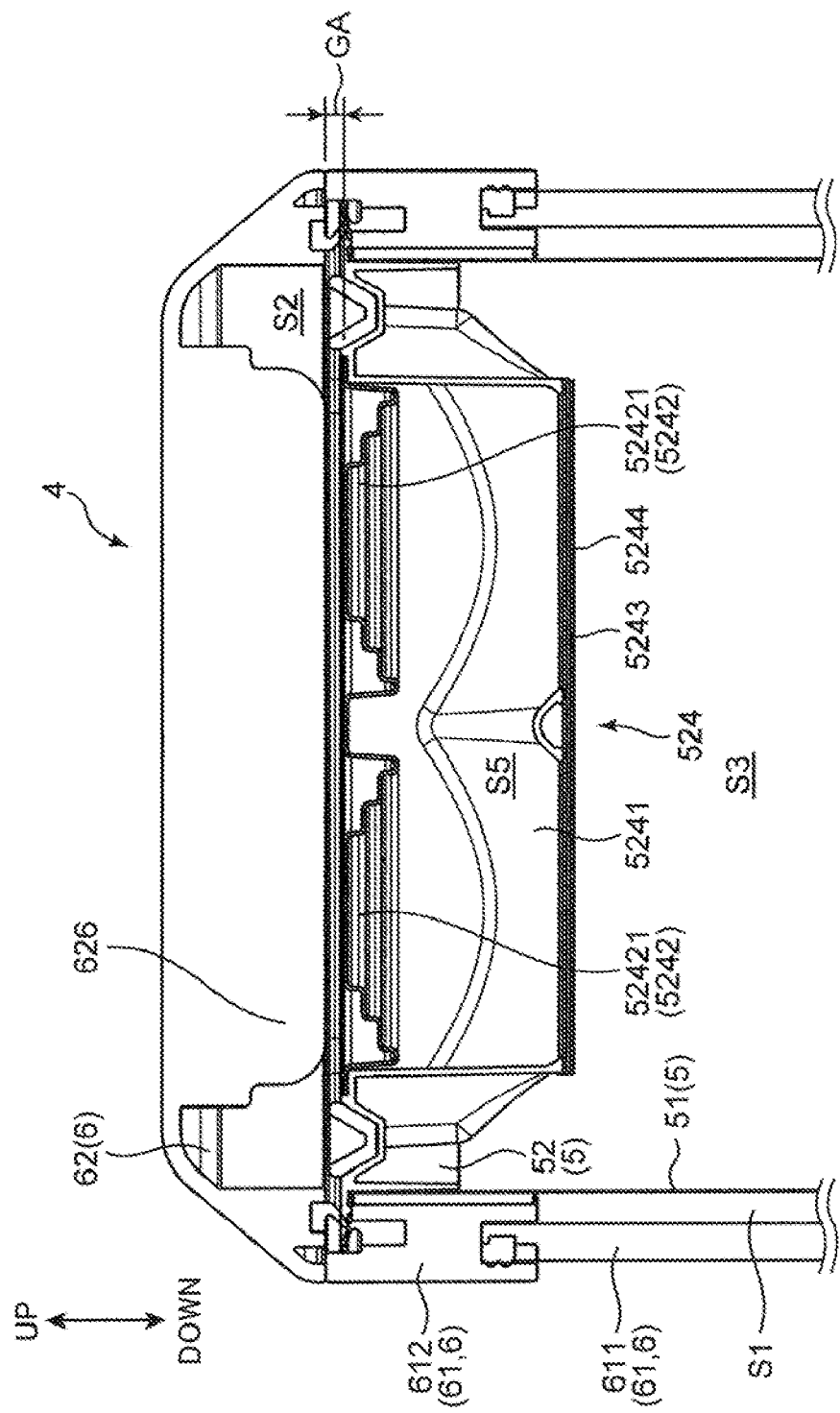
FIG. 5 is a partial cross-sectional view illustrating a main part of the waste liquid reservoir in an enlarged manner.

The waste liquid reservoir 4 includes: a liner 5 (waste liquid receiving receptacle) that receives the waste liquid WL; and a canister 6 (receptacle housing) that houses the liner 5. The configuration of the waste liquid reservoir 4 will be described in detail with reference to FIG. 2 to FIG. 5 in addition to FIG. 1. FIG. 2 to FIG. 4 are perspective views of the waste liquid reservoir 4, FIG. 2 illustrates a state where an opening and closing lid 62 of the canister 6 is disposed at a closed position. FIG. 3 illustrates a state where the opening and closing lid 62 is disposed at an open position. FIG. 4 illustrates a state where the liner 5 is removed from the canister 6. FIG. 5 is a cross-sectional view illustrating a main part of the waste liquid reservoir 4 in an enlarged manner.

The waste liquid reservoir 4 is disposed between the suction starting point portion 33 and the suction source 2 on the suction path defined by the suction path portion 3 such that a central axis J1 (FIG. 2) extends along an upward and downward direction (vertical direction) in a state where the liner 5 is housed in the canister 6.

<Configuration of Canister>

The canister 6 is a receptacle housing that houses the liner 5 described later. The canister 6 includes a housing body 61, an opening and closing lid 62, an opening and closing operation member 63, and a ventilation valve 64.

The housing body 61 forms a body portion of the canister 6 for housing the liner 5. The housing body 61 is formed in a bottomed cylindrical shape (bottomed housing shape) that is elongated along a housing axis extending in the vertical direction. The housing axis of the housing body 61 indicates a central axis of the housing body 61. The housing axis is disposed coaxially with the central axis J1 of the waste liquid reservoir 4, and extends in the vertical direction. As mainly illustrated in FIG. 4, the housing body 61 is formed in a bottomed cylindrical shape having a circular upper opening 6121H that opens upward at an upper end surface portion 6121. The housing body 61 houses the liner 5. Further, the housing body 61 defines a suction space S1 in which a negative pressure is generated by a suction force of the suction source 2 outside the liner 5 housed in the housing body 61 together with, that is, in cooperation with the opening and closing lid 62 described later.

In the present embodiment, the housing body 61 includes: a body portion 611 having a bottomed cylindrical shape; and an upper structural portion 612 that is formed of a cylindrical body joined to an upper end of the body portion 611 and defines the upper opening 6121H in the upper end surface portion 6121 of the housing body 61. The housing body 61 is integrally formed as a whole by joining the upper structural portion 612 to the upper end of the body portion 611.

The housing body 61 is formed of a hard synthetic resin having higher rigidity than the liner 5 described later. In the housing body 61, the body portion 611 and the upper structural portion 612 may be formed of the same synthetic resin or may be formed of different kinds of synthetic resins. In the present embodiment, the body portion 611 is formed of a colorless transparent synthetic resin having light transmissivity such that a storage state of the waste liquid WL in the liner 5 housed in the housing body 61 can be visually recognized. On the other hand, the upper structural portion 612 is formed of a synthetic resin or metal that is colored in consideration of design property of the canister 6.

As illustrated in FIG. 1, the upper structural portion 612 includes: a suction source connecting portion 6122; and an atmosphere opening portion 6123. The suction source connecting portion 6122 makes the suction space S1 and the first path member 31 of the suction path portion 3 communicate with each other. Accordingly, the suction source connecting portion 6122 defines an air discharge path 61221 serving as a flow path of air discharged from the suction space S1 by a suction force of the suction source 2. The air discharge path 61221 is formed in a peripheral wall of the upper structural portion 612 formed of a cylindrical body in a penetrating manner. The suction source connecting portion 6122 is connected to the first path member 31 of the suction path portion 3. With such a configuration, the air discharge path 61221 of the suction source connecting portion 6122 and the first path member 31 communicate with each other. Accordingly, by a suction force of the suction source 2, air is discharged in a direction directed from the suction space S1 toward the suction source 2 (an arrow H1 in FIG. 1) so that a negative pressure is generated in the suction space S1. The present invention is not limited to the configuration where the air discharge path 61221 is formed in the upper structural portion 612 of the housing body 61. The air discharge path 61221 may be formed in the opening and closing lid 62.

The atmosphere opening portion 6123 defines an air inflow path 61231 that makes the suction space S1 and an external space S4 communicate with each other thus forming a flow path through which air in the external space S4 flows into the suction space S1. The air inflow path 61231 is formed in the peripheral wall of the upper structural portion 612 formed of a cylindrical body in a penetrating manner. The present invention is not limited to the configuration where the air inflow path 61231 is formed in the upper structural portion 612 of the housing body 61. The air inflow path 61231 may be formed in the opening and closing lid 62. The ventilation valve 64 is disposed in the air inflow path 61231 of the atmosphere opening portion 6123. The ventilation valve 64 is a valve element that closes or opens the air inflow path 61231. In a state where the air inflow path 61231 is closed by the ventilation valve 64, a negative pressure state in the suction space S1 generated by an action of a suction force of the suction source 2 is maintained. On the other hand, in a state where the action of the suction force of the suction source 2 is stopped and the air inflow path 61231 is opened by the ventilation valve 64, air flows into the suction space S1 which is in a negative pressure from the external space S4 through the air inflow path 61231. As a result, the suction space S1 is opened to the atmosphere.

In the present embodiment, in the upper structural portion 612, the suction source connecting portion 6122 and the atmosphere opening portion 6123 have a positional relationship of point symmetry with respect to the center of the upper structural portion 612 (the center of the upper opening 6121H) which forms a point of symmetry. In other words, when the upper structural portion 612 is viewed from above, the suction source connecting portion 6122 and the atmosphere opening portion 6123 are arranged opposite to each other on an imaginary line that passes through the center of the upper structural portion 612 (the center of the upper opening 6121H).

As illustrated in FIG. 1 to FIG. 4, the upper structural portion 612 further includes a lid support portion 6124 and an operation support portion 6125. The lid support portion 6124 supports an opening and closing lid 62 described later. The lid support portion 6124 extends more radially outward than the body portion 611 when the housing body 61 is viewed from above. The operation support portion 6125 supports the opening and closing operation member 63 described later. In the same manner as the lid support portion 6124, the operation support portion 6125 extends more radially outward than the body portion 611 when the housing body 61 is viewed from above. In the upper structural portion 612, the lid support portion 6124 is disposed close to the suction source connecting portion 6122, and the operation support portion 6125 is disposed close to the atmosphere opening portion 6123. In the upper structural portion 612, the lid support portion 6124 and the operation support portion 6125 have a positional relationship of point symmetry with respect to the center of the upper structural portion 612 (the center of the upper opening 6121H) that forms a point of symmetry. In other words, when the upper structural portion 612 is viewed from above, the lid support portion 6124 and the operation support portion 6125 are arranged opposite to each other on an imaginary line that passes the center of the upper structural portion 612 (the center of the upper opening 6121H).

As illustrated in FIG. 4, the upper structural portion 612 further includes a first seal groove 6126. The first seal groove 6126 is a groove formed on an upper end surface portion 6121 of the upper structural portion 612 on a side opposite to a portion of the upper structural portion 612 that is joined to the body portion 611. The first seal groove 6126 is formed of a circular annular groove extending along an opening edge of the upper opening 6121H. A first seal member 6126A is fitted into the first seal groove 6126. The first seal member 6126A is a seal member made of an elastically deformable rubber material.

The opening and closing lid 62 is a lid that is supported by the lid support portion 6124 of the upper structural portion 612. The opening and closing lid 62 opens and closes the upper opening 6121H of the upper end surface portion 6121 of the upper structural portion 612. The opening and closing lid 62 is made of a hard synthetic resin having higher rigidity than the liner 5 in the same manner as the housing body 61. In the present embodiment, the opening and closing lid 62 is made of a synthetic resin colored in the same color as the upper structural portion 612 of the housing body 61.

As illustrated in FIG. 2 to FIG. 4, the opening and closing lid 62 includes a lid rotating shaft portion 621 extending in a direction orthogonal to the housing axis extending in the vertical direction of the housing body 61. The opening and closing lid 62 is supported by the lid support portion 6124 so as to be rotatable about the lid rotating shaft portion 621. By rotating the opening and closing lid 62 about the lid rotating shaft portion 621, the opening and closing lid 62 can be displaced between a closed position where the opening and closing lid 62 closes the upper opening 6121H of the upper structural portion 612, and an open position where the opening and closing lid 62 opens the upper opening 6121H. FIG. 2 illustrates a state where the opening and closing lid 62 is disposed at the closed position, and FIG. 3 illustrates a state where the opening and closing lid 62 is disposed at the open position. In a state where the opening and closing lid 62 is disposed at the closed position, the opening and closing lid 62 defines the suction space S1 outside the liner 5 housed in the housing body 61 in cooperation with the housing body 61, that is, in cooperation with the housing body 61. In a state where the opening and closing lid 62 is disposed at the closed position and the upper opening 6121H is closed by the opening and closing lid 62, the suction space S1 in the housing body 61 forms a sealed space. On the other hand, in a state where the opening and closing lid 62 is disposed at the open position and the upper opening 6121H is opened, the liner 5 can be inserted into and taken out from the housing body 61.

As illustrated in FIG. 2 to FIG. 4, the opening and closing lid 62 includes a shaft attachment portion 622, a cutout portion 623, a closing surface portion 624, a top surface portion 625, and a pressing portion 626. The opening and closing lid 62 is formed in a circular shape as viewed in a plan view except for the shaft attachment portion 622 and the cutout portion 623.

The shaft attachment portion 622 is a portion of the opening and closing lid 62 to which the lid rotating shaft portion 621 is attached. The opening and closing lid 62 is supported by the lid support portion 6124 of the upper structural portion 612 by way of the shaft attachment portion 622. The cutout portion 623 is a portion cut out inward from an outer peripheral edge of the opening and closing lid 62 toward the center 62S (FIG. 2). The cutout portion 623, in a state where the opening and closing lid 62 is disposed at the closed position, allows the exposure of a waste liquid introducing port 522 of a receptacle lid 52 described later of the liner 5 housed in the housing body 61 (see FIG. 2). In the opening and closing lid 62, the shaft attachment portion 622 and the cutout portion 623 have a positional relationship of point symmetry with respect to the center 62S of the opening and closing lid 62 that forms a point of symmetry. In other words, as viewed in a plan view of the opening and closing lid 62, the shaft attachment portion 622 and the cutout portion 623 are arranged opposite to each other on an imaginary line that passes the center 62S of the opening and closing lid 62.

The closing surface portion 624 is a portion that faces the upper opening 6121H formed in the upper end surface portion 6121 of the upper structural portion 612, and closes the upper opening 6121H in a state where the opening and closing lid 62 is disposed at the closed position. The closing surface portion 624 is formed in a shape where a portion of a circle is cut out by the cutout portion 623 as viewed in a plan view. As illustrated in FIG. 3 and FIG. 4, the closing surface portion 624 includes: a contact portion 6241 disposed slightly inside an outer peripheral edge of the closing surface portion 624; and a recessed portion 6242 that is recessed toward a top surface portion 625 side from an end edge of the contact portion 6241 on an inner side. Engaging hooks 6243 are formed on the closing surface portion 624 in the vicinity of the cutout portion 623 disposed at the outer peripheral edge of the closing surface portion 624. The engaging hooks 6243 engage with engaging portions 634 of the opening and closing operation member 63 described later.

In a state where the opening and closing lid 62 is disposed at the closed position, the recessed portions 6242 of the closing surface portion 624 defines an upper space S2 (FIG. 1) above the liner 5 housed in the housing body 61. The contact portion 6241 is formed in a shape that conforms with the outer peripheral edge of the closing surface portion 624. In a state where the opening and closing lid 62 is disposed at the closed position, the contact portion 6241 is brought into contact with the upper end surface portion 6121 of the upper structural portion 612 by way of a flange portion 521 of the receptacle lid 52 (described later) of the liner 5. As illustrated in FIG. 3 and FIG. 4, the contact portion 6241 includes a second seal groove 6241A. The second seal groove 6241A is a groove extending along the contact portion 6241, that is, extending along the outer peripheral edge of the closing surface portion 624. A second seal member 6241B is fitted into the second seal groove 6241A. The second seal member 6241B is a seal member made of an elastically deformable rubber material.

In a state where the opening and closing lid 62 is disposed at the closed position, although details will be described later, the second seal member 6241B is brought into pressure contact with the flange portion 521 of the receptacle lid 52 of the liner 5 from above, and the first seal member 6126A is brought into pressure contact with the flange portion 521 from below. In other words, the flange portion 521 is sandwiched between the first seal member 6126A and the second seal member 6241B in a state where the opening and closing lid 62 is disposed at the closed position. Accordingly, airtightness between the suction space S1 in the housing body 61 and the upper space S2 is maintained. In a state where the opening and closing lid 62 is disposed at the closed position, a plurality of through holes 5211 (FIG. 1 and FIG. 3) that are formed in the flange portion 521 of the receptacle lid 52 of the liner 5 are disposed more inside of pressure contact portions of the flange portion 521 where the first seal member 6126A and the second seal member 6241B are brought into pressure contact with the flange portion 521. The through holes 5211 allow the suction space S1 and the upper space S2 to communicate with each other. With such a configuration, a negative pressure is generated in the suction space S1 due to a suction force of the suction source 2, and a negative pressure is generated also in the upper space S2 due to the suction force of the suction source 2.

With respect to the opening and closing lid 62, the top surface portion 625 is a portion disposed on a side opposite to the closing surface portion 624 in a thickness direction. The top surface portion 625 is exposed to the outside in a state where the opening and closing lid 62 is disposed at the closed position. In the same manner as the closing surface portion 624, the top surface portion 625 is formed in a shape where a portion of a circle is cut out by the cutout portion 623 as viewed in a plan view. As illustrated in FIG. 2, the top surface portion 625 has an inclined portion 6251 around the cutout portion 623. In a state where the opening and closing lid 62 is disposed at the closed position, the inclined portion 6251 faces the waste liquid introducing port 522 exposed from the cutout portion 623 of the receptacle lid 52 of the liner 5. The inclined portion 6251 is inclined upward along with the increase of a distance from an end edge of the cutout portion 623. With such a configuration, when a medical worker such as a nurse or the like performs an operation of connecting the second path member 32 to the waste liquid introducing port 522, it is possible to suppress the occurrence of a phenomenon that the top surface portion 625 of the opening and closing lid 62 obstructs such an operation and hence, it is possible to improve operability of the connecting operation of the second path member 32.

As illustrated in FIG. 3 and FIG. 4, the pressing portion 626 is formed on the recessed portion 6242 of the closing surface portion 624 of the opening and closing lid 62. The pressing portion 626 is formed on the recessed portion 6242 in a protruding manner toward the inside opposite to the top surface portion 625. Although the details will be described later, the pressing portion 626 prevents the plastic deformation of the first covering member 5242 of a waste liquid treating agent storing portion 524 of the liner 5 toward an upper side due to a suction force generated by a negative pressure in the upper space S2 from becoming equal to or more than a specified value. Assume a case where a negative pressure is not generated in the upper space S2 in a state where the opening and closing lid 62 is disposed at the closed position. In this case, as illustrated in FIG. 5, a gap GA is formed between the pressing portion 626 and the first covering member 5242. That is, the pressing portion 626 is formed such that the pressing portion 626 is brought into contact with the first covering member 5242 when the first covering member 5242 is plastically deformed by the suction force generated by a negative pressure in the upper space S2 to an extent that the first covering member 5242 reaches the height position set preliminarily.

Next, the opening and closing operation member 63 is described with reference to FIG. 1 to FIG. 4. The opening and closing operation member 63 is a member that is supported by the operation support portion 6125 of the upper structural portion 612 of the housing body 61 and is provided for operating opening and closing of the opening and closing lid 62. Supporting of the opening and closing operation member 63 is not limited the supporting where the opening and closing operation member 63 is supported by the upper structural portion 612 of the housing body 61. The opening and closing operation member 63 may be supported by the opening and closing lid 62. The opening and closing operation member 63 is operated by a medical worker such as a nurse or the like when the opening and closing lid 62 is opened or closed. The opening and closing operation member 63 can change its posture between a closing holding posture in which the opening and closing operation member 63 maintains a state where the opening and closing lid 62 is disposed at the closed position by preventing opening of the opening and closing lid 62, and an opening allowing posture in which the opening of the upper opening 6121H is allowed in accordance with the displacement of the opening and closing lid 62 from the closed position to the open position.

In the same manner as the housing body 61 and the opening and closing lid 62, the opening and closing operation member 63 is formed of a hard synthetic resin having higher rigidity than the liner 5. In the present embodiment, the opening and closing operation member 63 is formed of a synthetic resin colored in a color different from colors of the upper structural portion 612 of the housing body 61 and the opening and closing lid 62. With such coloring, it is possible to easily distinguish the opening and closing operation member 63 from the upper structural portion 612 and the opening and closing lid 62.

The opening and closing operation member 63 includes an operation rotary shaft portion 631, a pressing operation portion 632, and the engaging portions 634.

The operation rotary shaft portion 631 is a shaft portion that extends in a direction orthogonal to the housing axis of the housing body 61, and extends parallel to the lid rotating shaft portion 621. The operation rotary shaft portion 631 has a function of rotatably supporting the opening and closing operation member 63 with respect to the operation support portion 6125 of the upper structural portion 612. The opening and closing operation member 63 is supported by the operation support portion 6125 so as to be rotatable about the operation rotary shaft portion 631. The opening and closing operation member 63 can change its posture between the closing holding posture and the opening allowing posture by its rotation about the operation rotary shaft portion 631.

A downward depressing force is applied to the pressing operation portion 632 by a pressing operation performed by a medical worker such as a nurse. The engaging portion 634 engages with the engaging hook 6243 of the opening and closing lid 62 in a state where the opening and closing operation member 63 takes the closing holding posture. In a state where the engaging portion 634 engages with the engaging hook 6243, a state where the opening and closing lid 62 is disposed at the closed position is maintained. When the pressing operation portion 632 is pushed down by applying a depressing force, the opening and closing operation member 63 rotates about the operation rotary shaft portion 631 so as to change its posture from the closing holding posture to the opening allowing posture. At this stage of the operation, the engagement state between the engaging portion 634 and the engaging hook 6243 is released. As a result, the opening and closing lid 62 can rotate from the closed position to the open position. On the other hand, in a state where no depressing force is applied to the pressing operation portion 632, the closing and holding posture of the opening and closing operation member 63 is maintained. At this stage of the operation, the engaging portion 634 and the engaging hook 6243 are engageable with each other. As a result, a state where the opening and closing lid 62 is disposed at the closed position can be maintained.

<Configuration of Liner>

Figure 6:
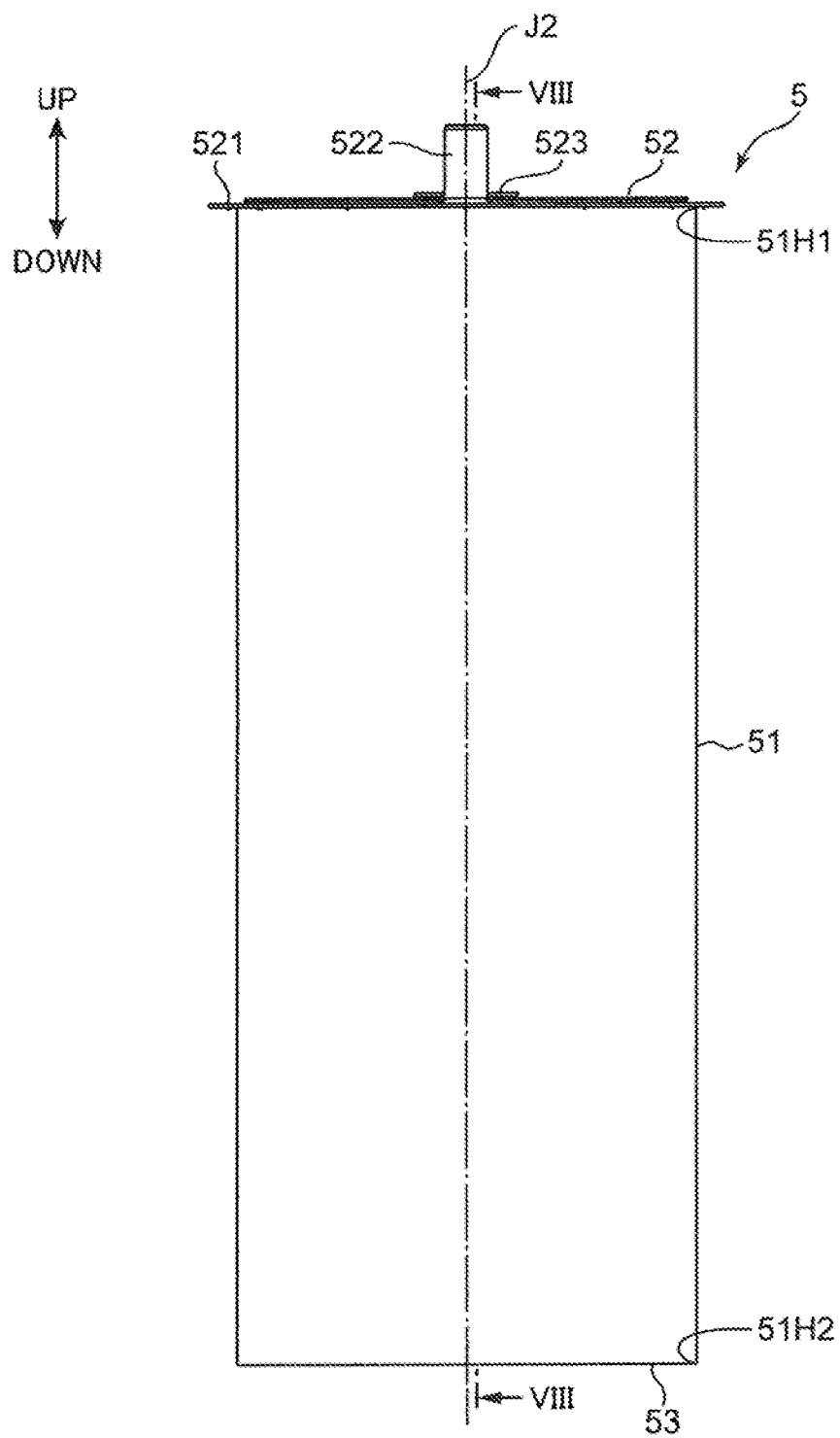
FIG. 6 is a view of the liner as viewed in a side view.
Figure 7:
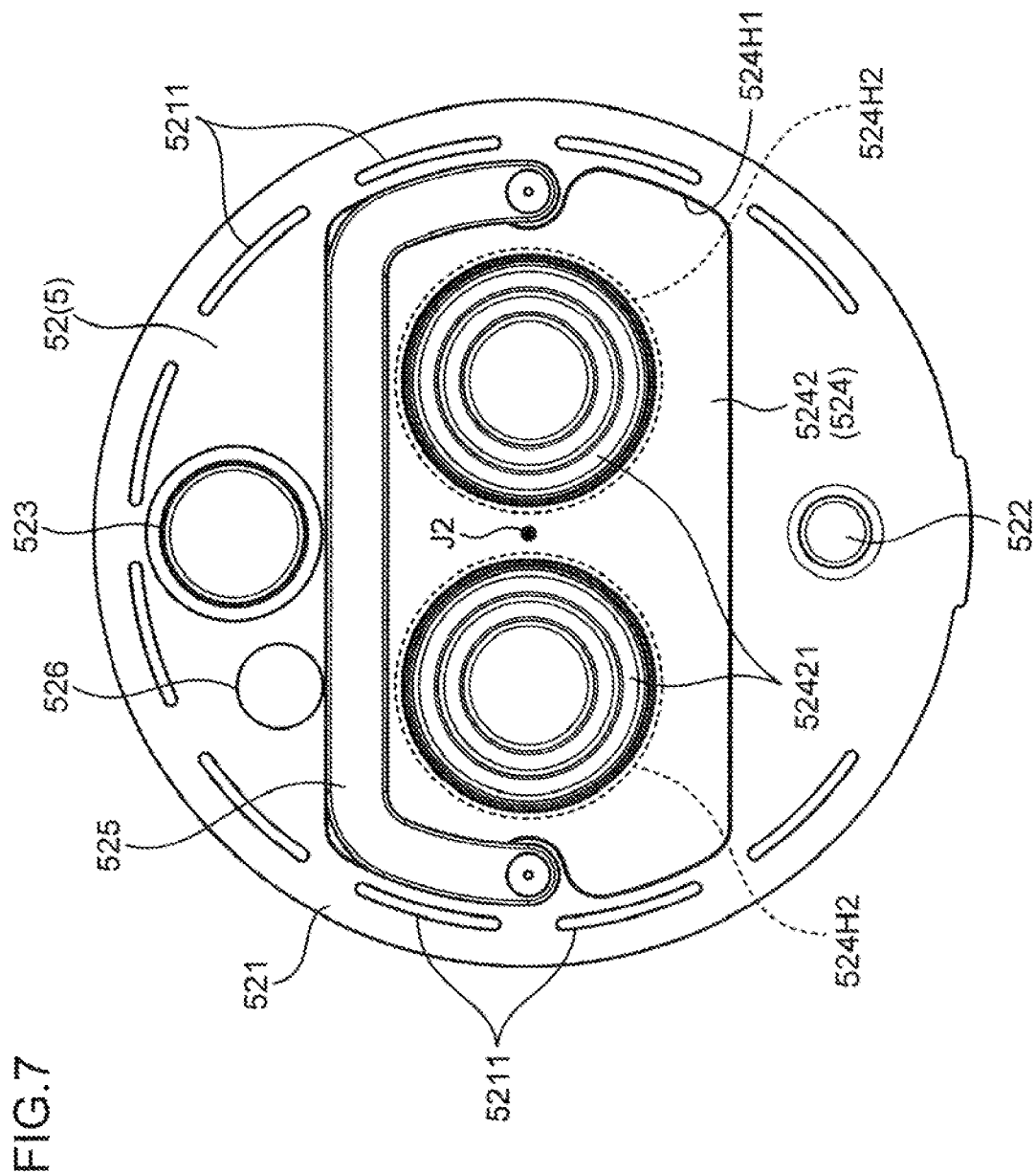
FIG. 7 is a view of the liner as viewed in a top plan view.
Figure 8:
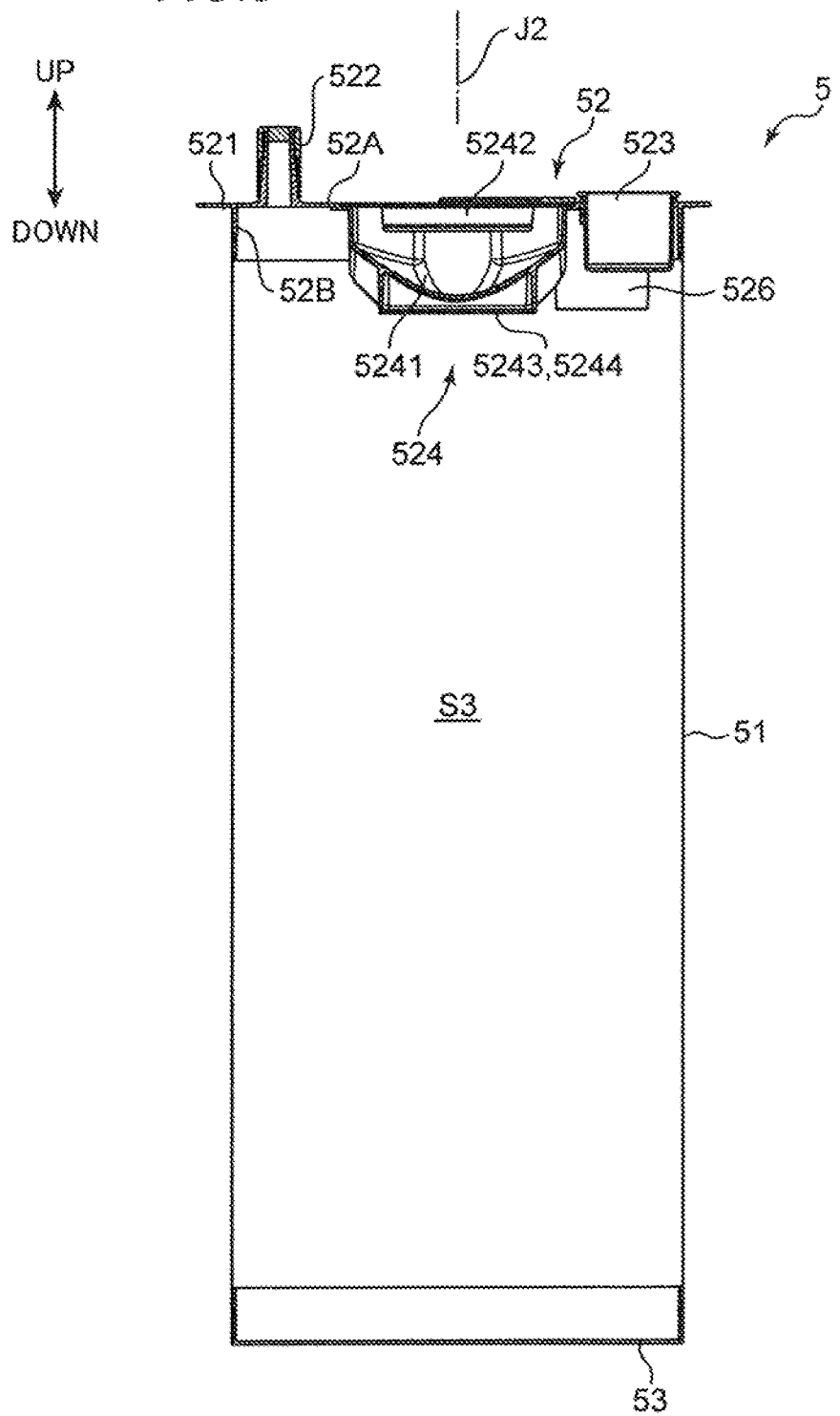
FIG. 8 is a cross-sectional view of the liner illustrated in FIG. 6 as viewed in a direction taken along line VIII-VIII.
Figure 9:
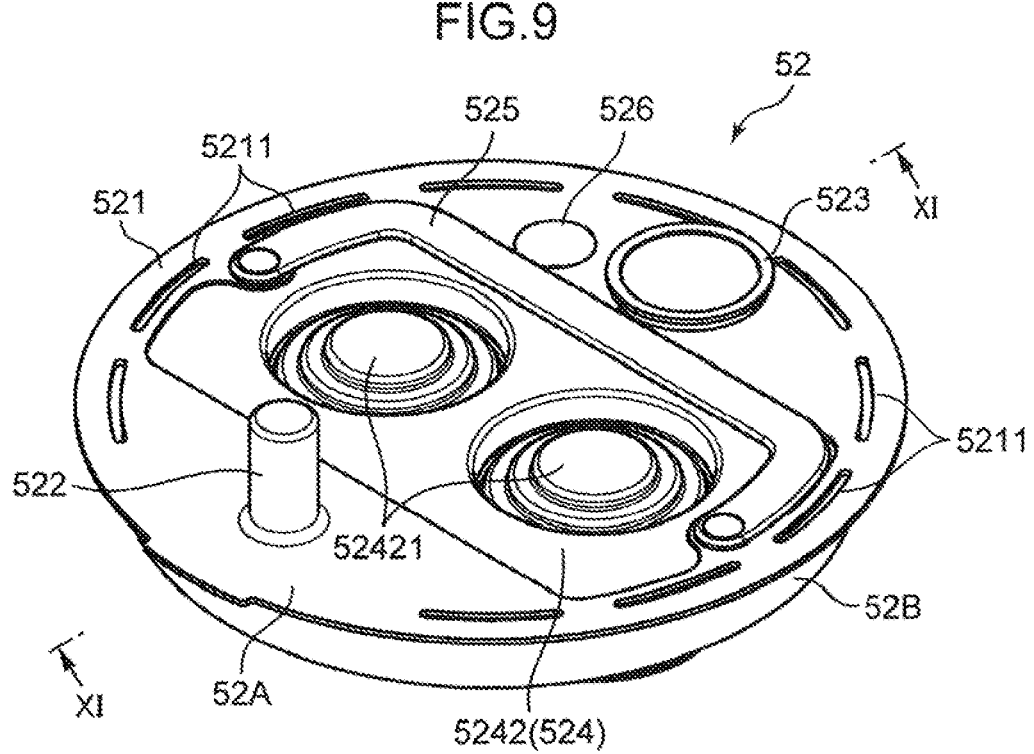
FIG. 9 is a perspective view illustrating a receptacle lid of the liner.
Figure 10:
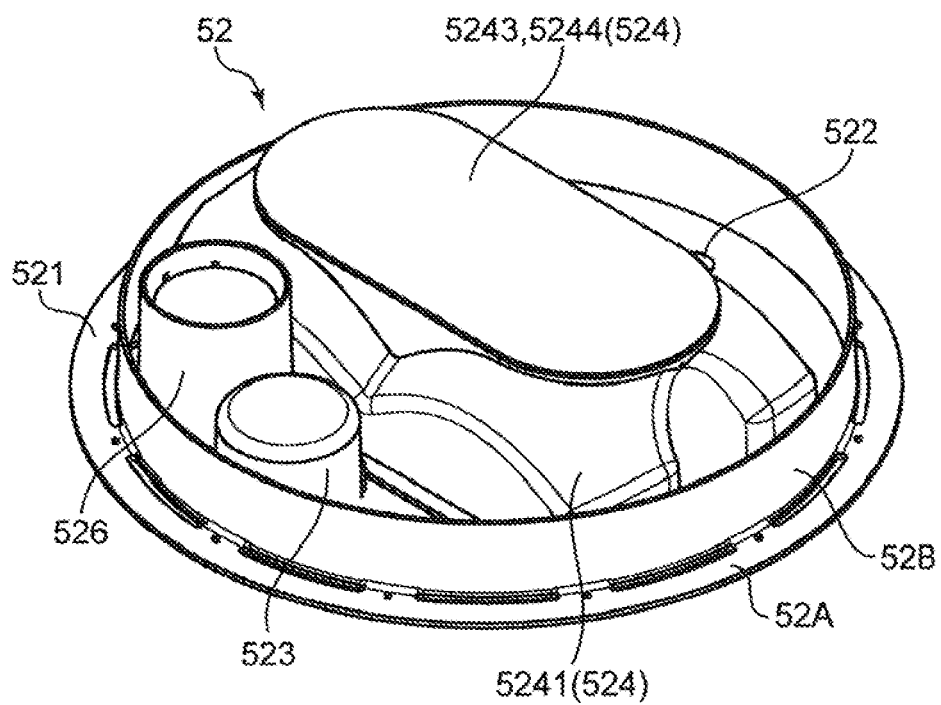
FIG. 10 is a perspective view illustrating the receptacle lid of the liner.
Figure 11:
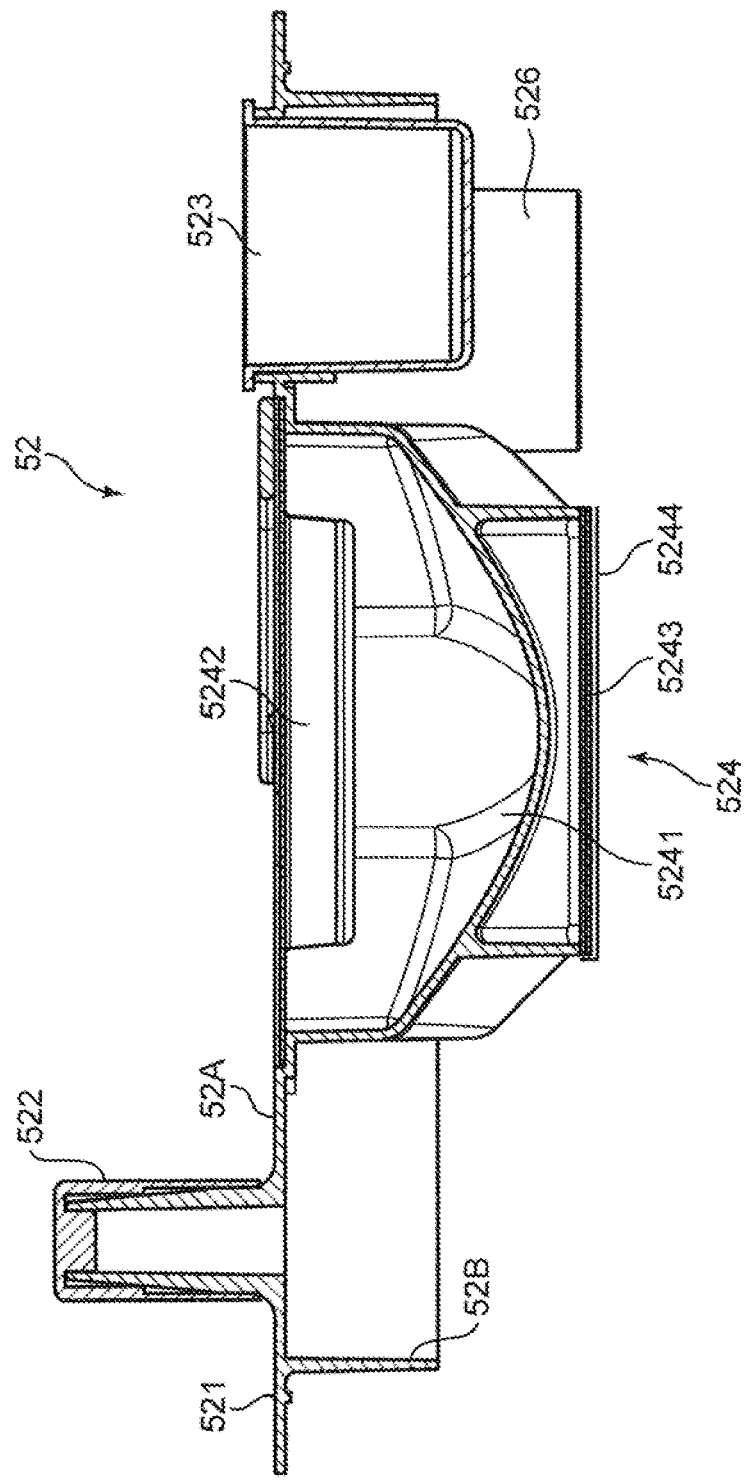
FIG. 11 is a cross-sectional view of the receptacle lid illustrated in FIG. 9 as viewed in a direction taken along line XI-XI.

Next, the liner 5 will be described with reference to FIG. 6 to FIG. 13 in addition to FIG. 1, and FIG. 3 to FIG. 5. FIG. 6 is a side view of the liner 5, FIG. 7 is a top plan view of the liner 5, and FIG. 8 is a cross-sectional view of the liner 5. FIG. 9 to FIG. 13 are views illustrating the receptacle lid 52 provided to the liner 5.

The liner 5 is a waste liquid receiving receptacle housed in the canister 6. When a negative pressure is generated in the suction space S1 and the upper space S2 of the canister 6, a negative pressure is generated in the liner 5. Accordingly, a waste liquid WL is sucked into the liner 5 from the suction starting point portion 33 and is received by the liner 5. The liner 5 includes a cylindrical body 51, the receptacle lid 52, and a bottom plate 53. The cylindrical body 51 is formed in a cylindrical shape having a peripheral wall that surrounds a cylindrical body axis J2, and has openings 51H1 and 51H2 at one end and the other end of the cylindrical body 51 in an axial direction (vertical direction) along the cylindrical body axis J2. The receptacle lid 52 closes the opening 51H1 on one end side of the cylindrical body 51. The bottom plate 53 closes the opening 51H2 on the other end side of the cylindrical body 51. The liner 5 is formed as an integral body as a whole by joining the receptacle lid 52 to one end of the cylindrical body 51 and by joining the bottom plate 53 to the other end of the cylindrical body 51. The liner 5 is housed in the canister 6 such that the cylindrical body axis J2 of the cylindrical body 51 extends in the vertical direction, one end side of the cylindrical body 51 faces upward, and the other end side of the cylindrical body 51 faces downward. That is, in a state where the liner 5 is housed in the canister 6, the cylindrical body 51 extends in the vertical direction, the receptacle lid 52 joined to one end of the cylindrical body 51 is disposed on an upper side, and the bottom plate 53 joined to the other end of the cylindrical body 51 is disposed on a lower side.

The cylindrical body 51 forms a body portion that defines a waste liquid receiving space S3 for receiving the waste liquid WL in the liner 5 in cooperation with the receptacle lid 52 and the bottom plate 53. The cylindrical body 51 is formed in a cylindrical shape elongated along the cylindrical body axis J2 extending in the vertical direction. The cylindrical body axis J2 of the cylindrical body 51 indicates the central axis of the cylindrical body 51. In a state where the liner 5 is housed in the canister 6, the cylindrical body axis J2 is disposed coaxially with the central axis J1 of the waste liquid reservoir 4 and extends in the vertical direction. The cylindrical body 51 is made of a synthetic resin having flexibility and having lower rigidity than the canister 6.

The cylindrical body 51 is formed of a synthetic resin having flexibility. Accordingly, the cylindrical body 51 can be deformed by compression in a state where the cylindrical body 51 is collapsed by applying a compressive force to the cylindrical body 51 along the cylindrical body axis J2. Due to the deformation of the cylindrical body 51 by compression, the liner 5 can be made compact. Accordingly, a space that the liner 5 occupies during storage or transportation of the liner 5 can be made small. In deforming the cylindrical body 51 by compression, it is sufficient to apply a compressive force to the cylindrical body 51 along the cylindrical body axis J2. However, it is desirable to apply the compressive force to the cylindrical body 51 while twisting the cylindrical body 51 about the cylindrical body axis J2. With such applying of the compressive force, it is possible to prevent a portion of the cylindrical body 51 from protruding outward in the radial direction in a mode after the cylindrical body 51 is deformed by compression and hence, it is possible to make the liner 5 compact more appropriately. In this case, a tensile force along the cylindrical body axis J2 is applied to the cylindrical body 51 in a deformed state by compression. Accordingly, the cylindrical body 51 is restored to a cylindrical shape elongated along the cylindrical body axis J2. In this manner, the liner 5 is set in the canister 6 in a state where the cylindrical body 51 is formed in a cylindrical shape. Accordingly, a state is brought about where the liner 5 is housed in the canister 6.

The bottom plate 53 is a member that closes the opening 51H2 formed in the other end side of the cylindrical body 51. The bottom plate 53 is formed in a disk shape, and is joined to the other end (lower end) of the cylindrical body 51 in the axial direction (vertical direction) so as to close the opening 51H2. The bottom plate 53 is formed of a hard synthetic resin having higher rigidity than the cylindrical body 51. The bottom plate 53 does not have flexibility unlike the cylindrical body 51. In the present embodiment, the bottom plate 53 is made of a colored synthetic resin so as to be easily distinguished from the cylindrical body 51.

The receptacle lid 52 is a lid that is formed in a circular shape in a plan view as viewed from above, and closes the opening 51H1 formed on one end side of the cylindrical body 51. The receptacle lid 52 is joined to one end (upper end) of the cylindrical body 51 in the axial direction (vertical direction) so as to close the opening 51H1. In the same manner as the bottom plate 53, the receptacle lid 52 is made of a hard synthetic resin having higher rigidity than the cylindrical body 51. The receptacle lid 52 does not have flexibility unlike the cylindrical body 51. In the present embodiment, the receptacle lid 52 is made of a synthetic resin colored in the same color as the bottom plate 53 so as to be easily distinguished from the cylindrical body 51.

In a state where the liner 5 is housed in the canister 6, the receptacle lid 52 defines the upper space S2 between the receptacle lid 52 and the opening and closing lid 62 of the canister 6 on an upper side of the cylindrical body 51. That is, the receptacle lid 52 is disposed facing the upper space S2 of the canister 6 in a state where the liner 5 is housed in the canister 6. In such a state, the receptacle lid 52 defines the waste liquid receiving space S3 for receiving the sucked waste liquid WL in cooperation with the cylindrical body 51 and the bottom plate 53 on a lower side of the upper space S2.

The receptacle lid 52 has: a disk-shaped base portion 52A in a plan view as viewed from above; and an insertion portion 52B having a circular cylindrical shape and extending vertically downward inside an outer peripheral edge of the base portion 52A on a lower surface of the base portion 52A. In the receptacle lid 52, the base portion 52A and the insertion portion 52B are integrally formed with each other. The receptacle lid 52 is joined to one end (upper end) of the cylindrical body 51 in a state where the insertion portion 52B is inserted into the cylindrical body 51 and an outer peripheral surface of the insertion portion 52B is brought into close contact with an inner peripheral surface of the cylindrical body 51.

In the receptacle lid 52, the base portion 52A includes a flange portion 521, a waste liquid introducing port 522, a waste liquid discharge port 523, a communication port 526, a waste liquid treating agent storing portion 524, and a grip member 525.

The flange portion 521 is a portion of the base portion 52A extending more radially outward than the insertion portion 52B in a state where the receptacle lid 52 is joined to one end of the cylindrical body 51. That is, the flange portion 521 extends radially outward with respect to the cylindrical body 51. The flange portion 521 is brought into contact with an upper end surface portion 6121 of the upper structural portion 612 of the housing body 61 in a state where the liner 5 is housed in the canister 6. Further, in a state where the opening and closing lid 62 of the canister 6 is disposed at the closed position, the flange portion 521 is sandwiched between the contact portion 6241 of the closing surface portion 624 of the opening and closing lid 62 and the upper end surface portion 6121 of the upper structural portion 612. That is, the flange portion 521 has a pressure contact portion that is sandwiched between the first seal member 6126A and the second seal member 6241B such that both the first seal member 6126A and the second seal member 6241B are brought into pressure contact with the pressure contact portion in a state where the opening and closing lid 62 is disposed at the closed position. As described above, the closing surface portion 624 of the opening and closing lid 62 has a shape in which a portion of the circle is cut out corresponding to the cutout portion 623. Accordingly, although the first seal member 6126A is brought into pressure contact with the lower surface of the flange portion 521 over the entire circumference, the second seal member 6241B is brought into pressure contact with the upper surface of the flange portion 521 except for a portion corresponding to the cutout portion 623. In other words, in the flange portion 521, the pressure contact portions with which both seal members consisting of the first seal member 6126A and the second seal member 6241B are brought into pressure contact are remaining portions excluding the portions corresponding to the cutout portion 623.

A plurality of through holes 5211 are formed in the flange portion 521 in a penetrating manner in the thickness direction (vertical direction). The plurality of through holes 5211 are disposed more inside than the pressure contact portion in the flange portion 521, and make the suction space S1 of the canister 6 and the upper space S2 communicate with each other. With such a configuration, a negative pressure is generated in the suction space S1 due to a suction force of the suction source 2, and a negative pressure is generated also in the upper space S2 due to the suction force of the suction source 2. The through holes 5211 are not formed in a portion of the flange portion 521 corresponding to the cutout portion 623.

The communication port 526 is a port that extends in the vertical direction, and is formed in the receptacle lid 52 in a penetrating manner more inside than the cylindrical body 51 in the radial direction in a state where the receptacle lid 52 is joined to one end of the cylindrical body 51. An upper end portion of the communication port 526 is disposed in the upper space S2 formed on the upper side of the liner 5 that is housed in the housing body 61 in a state where the opening and closing lid 62 of the canister 6 is disposed at the closed position. On the other hand, a lower end portion of the communication port 526 is disposed in the waste liquid receiving space S3 of the cylindrical body 51. That is, the communication port 526 makes the waste liquid receiving space S3 of the cylindrical body 51 corresponding to the inside of the liner 5 and the upper space S2 formed on the upper side of the liner 5 communicate with each other. With such a configuration, a negative pressure is generated also in the waste liquid receiving space S3 of the cylindrical body 51 when a negative pressure is generated in the suction space S1 and the upper space S2 due to a suction force of the suction source 2.

A water stop filter is disposed at a lower end portion of the communication port 526. In the liner 5, when a liquid level of the waste liquid WL received in the waste liquid receiving space S3 of the cylindrical body 51 reaches the water stop filter disposed at the lower end portion of the communication port 526, it is considered that the waste liquid receiving space S3 is fully filled with the waste liquid WL received by the waste liquid receiving space S3. The waste liquid discharge port 523 is a port that is formed in the receptacle lid 52 in a penetrating manner more inside in the radial direction than the cylindrical body 51 and extends in the vertical direction in a state where the receptacle lid 52 is joined to the upper end of the cylindrical body 51. The waste liquid discharge port 523 is a port for discharging the waste liquid WL received in the liner 5 (in the waste liquid receiving space S3 of the cylindrical body 51) in a state where the liner 5 is removed from the canister 6. The grip member 525 is attached to the receptacle lid 52. A medical worker such as a nurse can take out the liner 5 from the canister 6 by gripping the grip member 525.

The waste liquid introducing port 522 is a port that is formed in the receptacle lid 52 in a penetrating manner more inside the cylindrical body 51 in the radial direction and extends in the vertical direction in a state where the receptacle lid 52 is joined to one end of the cylindrical body 51. In the present embodiment, the waste liquid introducing port 522 and the waste liquid discharge port 523 have a symmetrical positional relationship with respect to an imaginary plane that includes the cylindrical body axis J2 of the cylindrical body 51. More desirably, the waste liquid introducing port 522 and the waste liquid discharge port 523 have a positional relationship of point symmetry with respect to the center of the receptacle lid 52 disposed on the cylindrical body axis J2 that forms a point of symmetry in a plan view of the receptacle lid 52 as viewed from above. In other words, in a plan view of the receptacle lid 52 as viewed from above, the waste liquid introducing port 522 and the waste liquid discharge port 523 are arranged opposite to each other on an imaginary line that passes the center of the receptacle lid 52.

The waste liquid introducing port 522 protrudes upward from the receptacle lid 52 so as to be exposed from the cutout portion 623 in a state where the opening and closing lid 62 of the canister 6 is disposed at the closed position. The waste liquid introducing port 522 is connected to the second path member 32 of the suction path portion 3. When a negative pressure is generated in the waste liquid receiving space S3 of the liner 5 corresponding to generation of a negative pressure in the suction space S1 and the upper space S2 due to a suction force of the suction source 2, the waste liquid introducing port 522 introduces the waste liquid WL sucked from the suction starting point portion 33 into the waste liquid receiving space S3. That is, when a negative pressure is generated in the waste liquid receiving space S3 of the liner 5 due to a suction force of the suction source 2, the waste liquid WL sucked from the suction starting point portion 33 flows through the second path member 32 and the waste liquid introducing port 522 (flows in the direction indicated by an arrow H2 in FIG. 1) and is received in the waste liquid receiving space S3 of the liner 5.

The waste liquid treating agent storing portion 524 is a portion of the receptacle lid 52 that contains a waste liquid treating agent for treating the waste liquid WL received in the waste liquid receiving space S3. The waste liquid treating agent storing portion 524 is disposed radially inside the cylindrical body 51 at the center of the receptacle lid 52, and is disposed inside the waste liquid introducing port 522, the waste liquid discharge port 523, and the communication port 526.

As a waste liquid treating agent that is stored in the waste liquid treating agent storing portion 524, a coagulant or a flocculant can be named. A coagulant is a treating agent capable of coagulating the waste liquid WL. As a coagulant, a solid coagulant in a powder form, in a granular form, or in a lump form or the like is used. However, in order to increase a contact area between a coagulant and the waste liquid WL as much as possible, it is desirable to use a coagulant in a powder form or a coagulant in a granular form. When a coagulant is added to the waste liquid WL received in the waste liquid receiving space S3 of the liner 5, the waste liquid WL is coagulated by the coagulant. On the other hand, a flocculant is a treating agent capable of flocculating components stored in the waste liquid WL to generate aggregates in the waste liquid receiving space S3 of the liner 5. Specifically, the flocculant flocculates red blood cells that are cell components stored in blood, or proteins or the like stored in plasma that is a liquid component. As the flocculant, a solid flocculant in a powder form, in a granular form, or in a lump form, or the like is used. However, in order to facilitate dispersion of a flocculant in the waste liquid WL, it is desirable to use a flocculant in a powder form or in a granular form. When a flocculant is added to the waste liquid WL received in the waste liquid receiving space S3 of the liner 5, components stored in the waste liquid WL are precipitated as aggregates in the waste liquid receiving space S3 by the flocculant. As a result, the waste liquid WL is separated into a supernatant liquid and the aggregates in the waste liquid receiving space S3.

The waste liquid treating agent storing portion 524 includes: a storing body 5241 that forms a body portion in which a waste liquid treating agent is stored; a first covering member 5242 and a second covering member 5243 that are joined to the storing body 5241; and a protective film 5244 that is disposed so as to cover the second covering member 5243.

The storing body 5241 includes: a first opening 524H1 that opens to face the upper space S2 of the canister 6; and a second opening 524H2 that is disposed opposite to the first opening 524H1 and opens to face the waste liquid receiving space S3 of the cylindrical body 51. The storing body 5241 defines a treating agent storing space S5 that stores a waste liquid treating agent between the first opening 524H1 and the second opening 524H2. In the storing body 5241, the second opening 524H2 forms a lead-out port for leading out a waste liquid treating agent that is stored in the treating agent storing space S5 to the waste liquid receiving space S3. The second opening 524H2 is formed with an opening area smaller than an opening area of the first opening 524H1. The storing body 5241 is formed of a portion that is recessed downward at the center of the base portion 52A of the receptacle lid 52. Accordingly, in a state where the receptacle lid 52 is joined to one end (upper end) of the cylindrical body 51, the storing body 5241 protrudes toward a waste liquid receiving space S3 side with respect to one end of the cylindrical body 51. In other words, the storing body 5241 is disposed in the waste liquid receiving space S3 of the cylindrical body 51. Accordingly, a portion of the receptacle lid 52 protruding upward is reduced and hence, a height of the liner 5 can be lowered as a whole. The storing body 5241 is integrally formed with the receptacle lid 52. Accordingly, the storing body 5241 is made of a hard synthetic resin.

The first covering member 5242 is a member joined to the storing body 5241 so as to cover the first opening 524H1. As illustrated in FIG. 3, the first covering member 5242 is exposed in a state where the opening and closing lid 62 of the canister 6 is disposed at the open position so that a negative pressure in the upper space S2 is released. In such a state, a depressing force for pushing the first covering member 5242 downward is applied by a medical worker such as a nurse.

The first covering member 5242 is made of a material (synthetic resin) that is plastically deformable in the vertical direction. That is, the first covering member 5242 is plastically deformed upward by a suction force in a state where a negative pressure is generated in the upper space S2 of the canister 6. On the other hand, in a state where the opening and closing lid 62 is disposed at the open position so that a negative pressure in the upper space S2 is released, the first covering member 5242 is plastically deformed downward by a downward depressing force generated by a medical worker such as a nurse.

As described above, the pressing portion 626 is disposed in the recessed portion 6242 of the opening and closing lid 62 that defines the upper space S2 of the canister 6. The first covering member 5242 is formed such that the first covering member 5242 is brought into contact with the pressing portion 626 when the first covering member 5242 is plastically deformed by a suction force accompanying a negative pressure generated in the upper space S2 to an extent that the first covering member 5242 reaches the height position set preliminarily. With such a configuration, the plastic deformation of the first covering member 5242 toward the upper side due to a suction force accompanying a negative pressure in the upper space S2 is prevented from becoming equal to or more than the specified value. Further, in a case where a negative pressure is not generated in the upper space S2 in a state where the opening and closing lid 62 is disposed at the closed position, a protrusion length of the pressing portion 626 with respect to the recessed portion 6242 is set such that a gap GA is formed between the pressing portion 626 and the first covering member 5242 (see FIG. 5). That is, when the opening and closing lid 62 rotates from the open position toward the closed position in a state where the liner 5 is housed in the canister 6, the contacting of the pressing portion 626 with the first covering member 5242 is avoided. Accordingly, it is possible to prevent the first covering member 5242 from being damaged by an opening and closing operation of the opening and closing lid 62.

The second covering member 5243 is a member joined to the storing body 5241 so as to cover the second opening 524H2. Unlike the first covering member 5242, the second covering member 5243 is made of a material that does not cause plastic deformation as much as possible. The second covering member 5243 is made of paper or the like, for example. The second covering member 5243 is not plastically deformed by a suction force in a state where a negative pressure is generated in the waste liquid receiving space S3 of the cylindrical body 51. The second covering member 5243 is broken without being plastically deformed when the depressing force is applied to the first covering member 5242. That is, the second covering member 5243 is broken in such a manner that, when a depressing force that pushes the first covering member 5242 downward is applied to the first covering member 5242, the depressing force is transmitted to the second covering member 5243 by way of a waste liquid treating agent so that the second covering member 5243 is broken. When the second covering member 5243 is broken, the covering of the second opening 524H2 by the second covering member 5243 is released. Accordingly, a waste liquid treating agent stored in the treating agent storing space S5 of the storing body 5241 is added into the waste liquid receiving space S3 of the cylindrical body 51 through the second opening 524H2.

Figure 12:
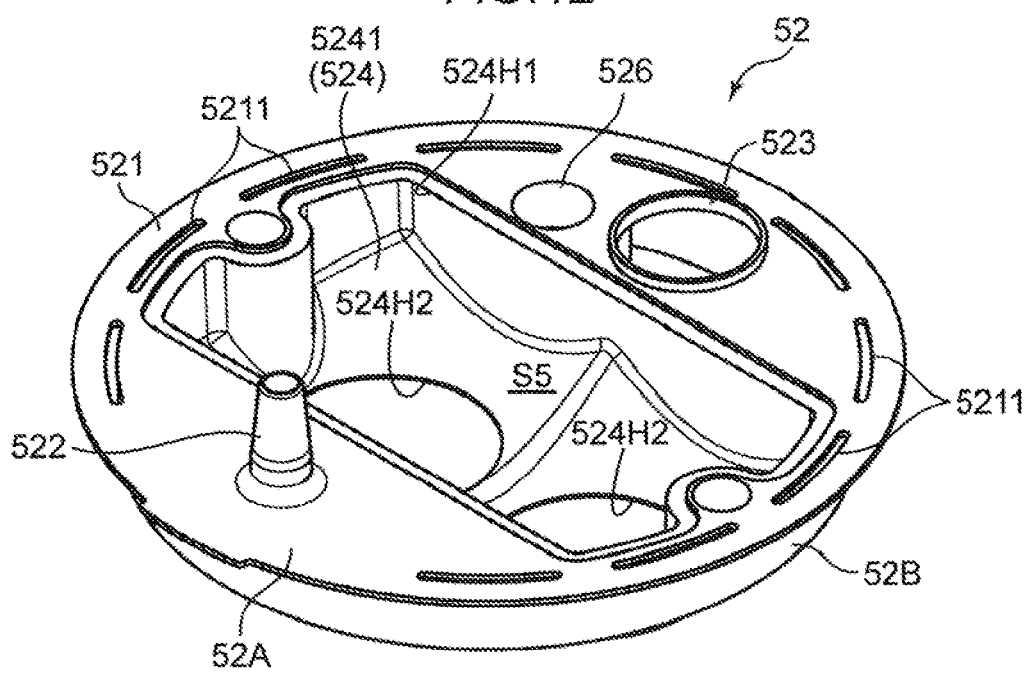
FIG. 12 is a perspective view of the receptacle lid in a state where a first covering member and a second covering member of a waste liquid treating agent storing portion are removed from the receptacle lid.
Figure 13:
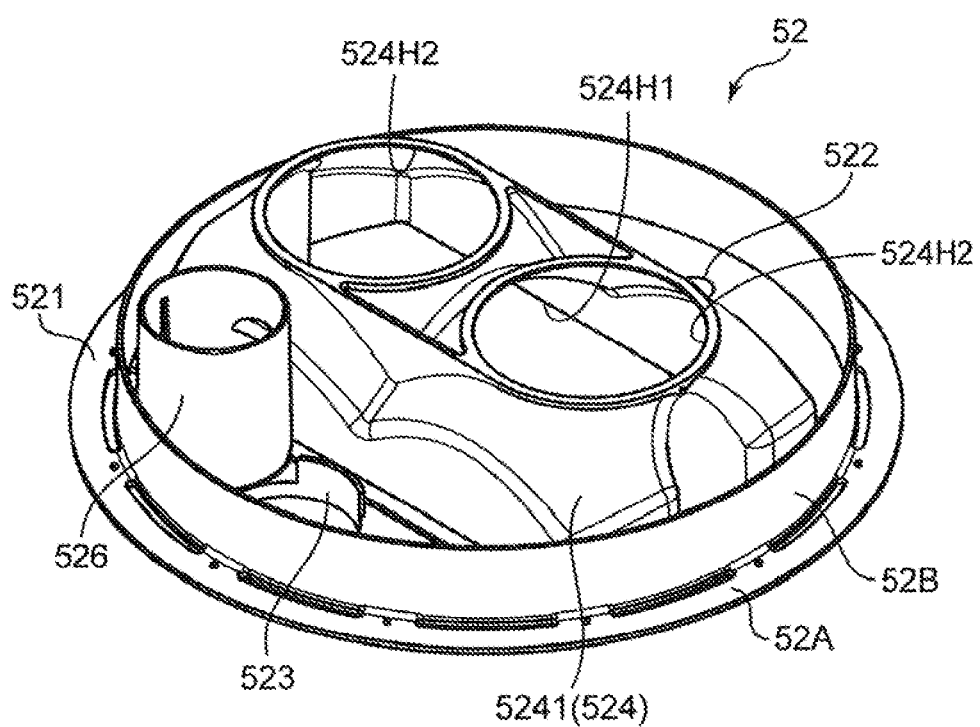
FIG. 13 is a perspective view of the receptacle lid illustrating a state where the first covering member and the second covering member of the waste liquid treating agent storing portion are removed from the receptacle lid.

As illustrated in FIG. 12 and FIG. 13, the storing body 5241 may be configured to have a plurality of second openings 524H2. In this case, the second covering member 5243 may be individually provided to each of the plurality of second openings 524H2, or one second covering member 5243 may be provided such that one second covering member 5243 covers the plurality of second openings 524H2 as a whole.

The second covering member 5243 is configured to restrict passing of the waste liquid WL received in the waste liquid receiving space S3 of the cylindrical body 51 into the treating agent storing space S5. That is, the second covering member 5243 has no through hole that makes the waste liquid receiving space S3 and the treating agent storing space S5 communicate with each other. As a result, it is possible to prevent deterioration of a waste liquid treating agent stored in the treating agent storing space S5 due to contacting of the waste liquid treating agent with the waste liquid WL.

Further, the first covering member 5242 includes pressing position guide portions 52421 serving as marks indicating positions at which the depressing force is applied the first covering member 5242 by a medical worker such as a nurse. The number of pressing position guide portions 52421 provided to the first covering member 5242 corresponds to the number of the second openings 524H2 of the storing body 5241. For example, when two second openings 524H2 are formed in the storing body 5241, two pressing position guide portions 52421 are provided correspondingly. In the first covering member 5242, as illustrated in FIG. 7, the pressing position guide portions 52421 are disposed at positions just above the second openings 524H2. Accordingly, when a depressing force that pushes the first covering member 5242 downward is applied using the pressing position guide portions 52421 as marks, the depressing force is effectively transmitted to the second covering member 5243. Accordingly, when a depressing force is applied to the first covering member 5242, the second covering member 5243 is broken with more certainty. As a result, a waste liquid treating agent can be appropriately added into the waste liquid receiving space S3 of the cylindrical body 51 through the second openings 524H2.

The protective film 5244 is a member that is formed so as to cover the second covering member 5243 from a waste liquid receiving space S3 side. The protective film 5244 protects the second covering member 5243. The protective film 5244 has a function of protecting the second covering member 5243. That is, in a state where the cylindrical body 51 is deformed by compression during storage, transportation or the like of the liner 5, it is possible to prevent the occurrence of a phenomenon that a portion of the cylindrical body 51 is brought into contact with the second covering member 5243 so that the second covering member 5243 is broken. The protective film 5244 is fixed to the storing body 5241 such that the protective film 5244 is opened by a weight of a waste liquid treating agent. Accordingly, when the second covering member 5243 is broken by an action of a depressing force applied to the first covering member 5242, the protective film 5244 does not obstruct discharging of a waste liquid treating agent through the second openings 524H2.

In the liner 5 having the above-mentioned configuration, corresponding to the generation of a negative pressure in the suction space S1 of the canister 6 and in the upper space S2 by a suction force of the suction source 2, a negative pressure is generated also in the waste liquid receiving space S3 of the cylindrical body 51. Accordingly, the sucked waste liquid WL is received in the waste liquid receiving space S3. In such an operation, in the waste liquid treating agent storing portion 524, the first covering member 5242 that covers the first openings 524H1 that open so as to face the upper space S2 is plastically deformed upward by a suction force caused by a negative pressure in the upper space S2. Accordingly, the second covering member 5243 that cover the second openings 524H2 formed in the storing body 5241 does not receive a force from above. Accordingly, the breaking of the second covering member 5243 is restricted. As a result, it is possible to prevent a waste liquid treating agent from being discharged from the treating agent storing space S5 of the storing body 5241 during an operation of sucking the waste liquid WL into the waste liquid receiving space S3 of the liner 5.

On the other hand, when a depressing force that pushes the first covering member 5242 downward is applied to the first covering member 5242 in a state where the opening and closing lid 62 of the canister 6 is opened so that a negative pressure in the upper space S2 is released, the depressing force is transmitted to the second covering member 5243 by way of a waste liquid treating agent. When the second covering member 5243 is broken due to such an operation, the covering of the second openings 524H2 by the second covering member 5243 is released. As a result, a waste liquid treating agent stored in the treating agent storing space S5 of the storing body 5241 is added into the waste liquid receiving space S3 of the cylindrical body 51 through the second openings 524H2.

Although the embodiment of the present invention has been described heretofore, the present invention is not limited to such an embodiment. For example, the following modifications can be adopted.

Figure 14:
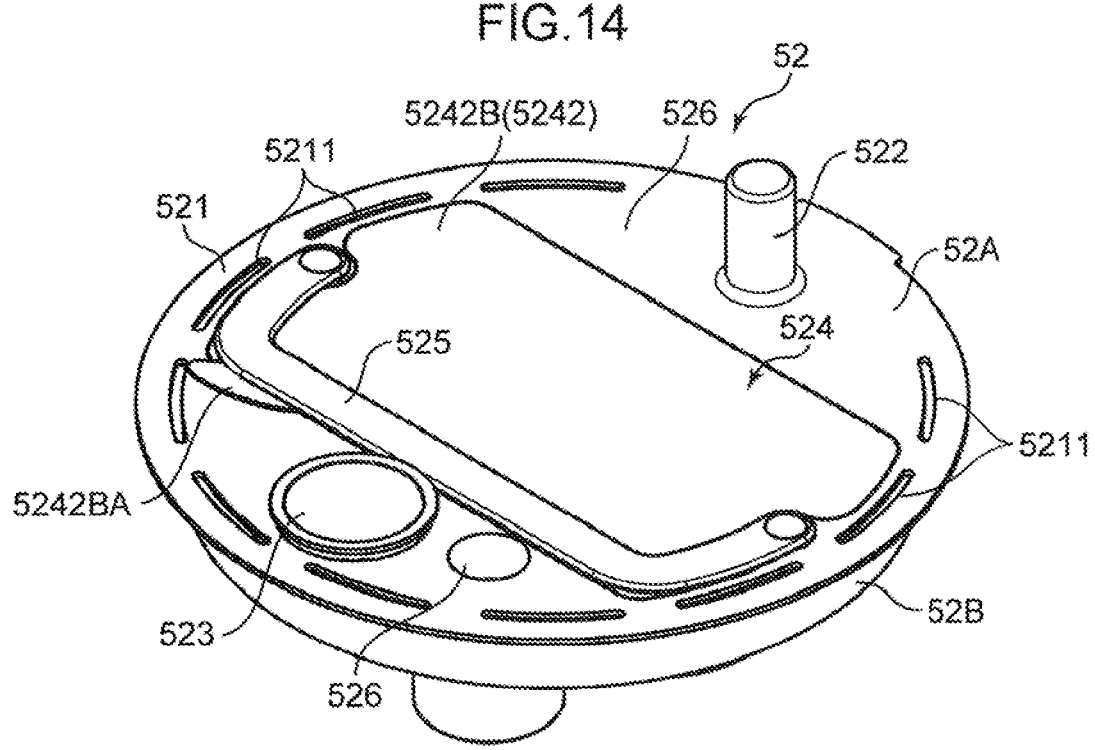
FIG. 14 is a perspective view illustrating a modification of the first covering member of the waste liquid treating agent storing portion.

In the above embodiment, the case has been described where the first covering member 5242 that forms the waste liquid treating agent storing portion 524 has a one-layer structure. However, the present invention is not limited to such a configuration. The first covering member 5242 may be configured to have a laminated structure including a lower layer film 5242A and an upper layer film 5242B as illustrated in FIG. 14 to FIG. 16.

In the first covering member 5242 having the laminated structure, the lower layer film 5242A is a layer joined to the storing body 5241 so as to cover the first opening 524H1, and the upper layer film 5242B is a layer laminated to the lower layer film 5242A. As described above, by forming the first covering member 5242 into the laminated structure, it is possible to enhance the degree of freedom in designing with respect to plastic deformation of the first covering member 5242 to the upper side due to a suction force accompanying a negative pressure in the upper space S2, and with respect to plastic deformation of the first covering member 5242 to the lower side due to applying of the depressing force to the first covering member 5242.

The upper layer film 5242B has a grip portion 5242BA, and the upper layer film 5242B can be peeled off from the lower layer film 5242A while gripping the grip portion 5242BA. A plurality of through holes 5242C are formed in the lower layer film 5242A.

For example, assume a case where a flocculant is used as a waste liquid treating agent to be added to the waste liquid WL received in the waste liquid receiving space S3 of the cylindrical body 51. In this case, when a flocculant is added to the waste liquid WL received in the waste liquid receiving space S3, components stored in the waste liquid WL are precipitated as aggregates in the waste liquid receiving space S3 by the flocculant. As a result, the waste liquid WL is separated into a supernatant liquid and the aggregates in the waste liquid receiving space S3. In discharging such a supernatant liquid, it is sufficient to expose the lower layer film 5242A having the plurality of through holes 5242C by peeling off the upper layer film 5242B from the lower layer film 5242A (see FIG. 16). Accordingly, a supernatant liquid can be discharged by filtering where only the supernatant liquid is allowed to pass through the through holes 5242C so that the supernatant liquid is separated from the aggregates.

The above-mentioned specific embodiments mainly include the inventions having the following configurations.

According to an aspect of the present invention, there is provided a waste liquid receiving receptacle housed in a receptacle housing. The receptacle housing includes a bottomed container-shaped housing body having an upper opening that opens upward, and an opening and closing lid supported by the housing body so s to be capable of opening and closing the upper opening, the waste liquid receiving receptacle being capable of receiving a predetermined waste liquid. The waste liquid receiving receptacle includes: a cylindrical body disposed in the housing body and having an opening on an upper side of the cylindrical body; a receptacle lid joined to an upper end of the cylindrical body, defining an upper space between the receptacle lid and the opening and closing lid on an upper side of the cylindrical body, and defining a waste liquid receiving space that receives a waste liquid sucked by a negative pressure generated in the waste liquid receiving space by communicating with the upper space in cooperation with the cylindrical body on a lower side of the upper space; and a waste liquid treating agent storing portion disposed on the receptacle lid, the waste liquid treating agent storing portion configured to store a waste liquid treating agent for treating a waste liquid received in the waste liquid receiving space. The waste liquid treating agent storing portion includes: a storing body having a first opening opened to face the upper space and a second opening opened to face the waste liquid receiving space, the storing body defining a treating agent storing space for storing the waste liquid treating agent between the first opening and the second opening; a first covering member joined to the storing body so as to cover the first opening; and a second covering member jointed to the storing body so as to cover the second opening. The first covering member is made of a material that plastically deforms upward by a suction force in a state where a negative pressure is generated in the upper space, and plastically deforms downward by a depressing force that pushes the first covering member downward in a state where the opening and closing lid is opened and the negative pressure in the upper space is released. The second covering member is made of a material that is not plastically deformed by a suction force in a state where a negative pressure is generated in the waste liquid receiving space and is broken without being plastically deformed in a case where the depressing force is applied to the first covering member.

According to this waste liquid receiving receptacle, in response to the generation of a negative pressure in the upper space defined on the upper side of the cylindrical body between the waste liquid receiving receptacle and the opening and closing lid of the receptacle housing, a negative pressure is generated in the waste liquid receiving space defined by the cylindrical body and the receptacle lid on the lower side of the upper space. Accordingly, the sucked waste liquid is received in the waste liquid receiving space. At this stage of the operation, in the waste liquid treating agent storing portion, the first covering member that covers the first opening opened to face the upper space is plastically deformed upward by a suction force caused by a negative pressure in the upper space. Accordingly, the second covering member that covers the second opening of the storing body does not receive a force from above and hence, the breaking of the second covering member is restricted. Accordingly, it is possible to prevent a waste liquid treating agent from being discharged from the treating agent storing space of the storing body during sucking a waste liquid into the waste liquid receiving space of the waste liquid receiving receptacle.

On the other hand, when a depressing force that pushes the first covering member downward is applied to the first covering member in a state where the opening and closing lid of the receptacle housing is opened so that a negative pressure in the upper space is released, the depressing force is transmitted to the second covering member by way of the waste liquid treating agent. Accordingly, when the second covering member is broken, the covering of the second opening by the second covering member is released. As a result, a waste liquid treating agent stored in the treating agent storing space of the storing body is added into the waste liquid receiving space of the cylindrical body through the second opening.

In the above-described waste liquid receiving receptacle, the second covering member may be configured to restrict passing of the waste liquid received in the waste liquid receiving space toward the treating agent storing space.

In this mode, by the second covering member, it is possible to restrict passing of a waste liquid received in the waste liquid receiving space of the cylindrical body from the waste liquid receiving space to the waste liquid treating agent storing space of the waste liquid treating agent storing portion. Accordingly, it is possible to prevent deterioration of a waste liquid treating agent stored in the treating agent storing space caused by contacting of the waste liquid treating agent with the waste liquid.

In the waste liquid receiving receptacle described above, in the storing body, the second opening may be formed with an opening area smaller than an opening area of the first opening, and the first covering member may have a pressing position guide portion, the pressing position guide portion being a portion serving as a mark of a position at which a depressing force is applied, the pressing position guide portion being disposed at a position just above the second opening.

In this mode, in the first covering member, the pressing position guide portion is disposed at the position just above the second opening covered by the second covering member. Accordingly, when a depressing force that pushes the first covering member downward is applied using the pressing position guide portion as a mark, the depressing force is effectively transmitted to the second covering member. Accordingly, when a depressing force is applied to the first covering member, the second covering member is broken with more certainty and hence, a waste liquid treating agent can be appropriately added into the waste liquid receiving space of the cylindrical body through the second openings.

In the above-described waste liquid receiving receptacle, the first covering member may be formed of a laminated structure that includes: a lower layer film joined to the storing body so as to cover the first opening; and an upper layer film adhesively laminated to the lower layer film.

In this mode, the first covering member is formed of the laminated structure and hence, it is possible to enhance the degree of freedom in designing with respect to plastic deformation of the first covering member, that is, the plastic deformation of the first covering member toward the upper side due to a suction force accompanying a negative pressure in the upper space and plastic deformation of the first covering member toward the lower side due to applying of the depressing force to the first covering member.

In the waste liquid receiving receptacle, the upper layer film may be configured to be peeled off from the lower layer film, and the lower layer film may have a plurality of through holes.

For example, assume a case where a flocculant is used as a waste liquid treating agent to be added to a waste liquid received in the waste liquid receiving space of the cylindrical body. In this case, when the flocculant is added to the waste liquid received in the waste liquid receiving space, components stored in the waste liquid are precipitated as aggregates in the waste liquid receiving space by the flocculant. As a result, the waste liquid is separated into a supernatant liquid and the aggregates in the waste liquid receiving space. In discharging such a supernatant liquid, it is sufficient to expose the lower layer film having the plurality of through holes by peeling off the upper layer film from the lower layer film. Accordingly, a supernatant liquid can be discharged by filtering where only the supernatant liquid is allowed to pass through the through holes so that the supernatant liquid is separated from the aggregates.

In the above-described waste liquid receiving receptacle, the storing body may be configured to protrude toward a waste liquid receiving space side with respect to an upper end of the cylindrical body.

In this mode, in a state where the receptacle lid is joined to the upper end of the cylindrical body, the storing body protrudes toward the waste liquid receiving space side of the cylindrical body. Accordingly, a portion of the receptacle lid protruding upward is reduced and hence, a height of the waste liquid receiving receptacle can be reduced as a whole.

According to another aspect of the present invention, there is provided a waste liquid reservoir including: a receptacle housing including: a bottomed container-shaped housing body having an upper opening that opens upward; and an opening and closing lid supported by the housing body so as to be capable of opening and closing the upper opening; and the above-mentioned waste liquid receiving receptacle housed in the receptacle housing and being capable of receiving a predetermined waste liquid.

In the waste liquid reservoir described above, in the receptacle housing the opening and closing lid includes a pressing portion that restricts upward plastic deformation of the first covering member in the waste liquid receiving receptacle due to a suction force accompanying a negative pressure in the upper space from becoming equal to or more than a specified value.

In the above-described waste liquid reservoir, the pressing portion is disposed so as to be brought into contact with the first covering member in a case where the first covering member is plastically deformed by the suction force accompanying the negative pressure in the upper space to an extent that the first cover member reaches a height position set preliminarily.

According to the waste liquid reservoir, the first covering member is brought into contact with the pressing portion when the first covering member is plastically deformed by a suction force accompanying a negative pressure in the upper space to an extent that the first covering member reaches the height position set preliminarily. Accordingly, when the first covering member is plastically deformed upward by a suction force accompanying a negative pressure in the upper space, by the pressing portion, it is possible to suppress the occurrence of a phenomenon that the plastic deformation of the first covering member becomes equal to or more than the specific value so that the first covering member is excessively deformed.

A waste liquid suction system according to still another aspect of the present invention is a system configured to suck a predetermined waste liquid and to reserve the sucked waste liquid. The waste liquid suction system includes: a suction source; a suction path portion forming a suction path from a suction starting point portion serving as a suction starting point in sucking the waste liquid to the suction source; and the above-mentioned waste liquid reservoir disposed between the suction starting point portion and the suction source on the suction path, the waste liquid reservoir configured to reserve the waste liquid sucked from the suction starting point portion due to a suction force of the suction source.

As has been described heretofore, according to the present invention, it is possible to provide the waste liquid receiving receptacle including the waste liquid treating agent storing portion that can prevent a waste liquid treating agent from being discharged from the waste liquid treating agent storing portion during sucking a waste liquid, the waste liquid reservoir including the same, and the waste liquid suction system.

The invention claimed is:

1. A waste liquid receptacle configured to be housed in a receptacle housing, the receptacle housing including a housing body having an upper opening that opens upward, and an openable and closable lid supported by the housing body so as to be capable of opening and closing the upper opening, the waste liquid receptacle being capable of receiving a waste liquid, the waste liquid receptacle comprising:
 a cylindrical body configured to be disposed in the housing body and having an opening on an upper side of the cylindrical body;
 a receptacle lid joined to an upper end of the cylindrical body, configured to define an upper space between the receptacle lid and the openable and closable lid on the upper side of the cylindrical body, and defining a waste liquid receipt space for receiving the waste liquid which has been sucked by a first negative pressure generated in the waste liquid receipt space by communicating with the upper space in cooperation with the cylindrical body on a lower side of the upper space; and
 a waste liquid treatment agent storage portion disposed on the receptacle lid, the waste liquid treatment agent storage portion being configured to store a waste liquid treatment agent for treating the waste liquid which has been received in the waste liquid receipt space, wherein the waste liquid treatment agent storage portion includes:
 a storing storage body having a first opening facing the upper space and a second opening facing the waste liquid receipt space, the storage body defining a treatment agent storage space for storing the waste liquid treatment agent between the first opening and the second opening;
 a first cover member joined to the storage body so as to cover the first opening; and
 a second cover member jointed to the storage body so as to cover the second opening,
 wherein:
 the first cover member is made of a material that is configured to: (i) be plastically deformed upward by a first suction force from the treatment agent storage space to the upper space in a state where a second negative pressure is generated in the upper space; and (ii) plastically deform downward by a depressing force against the first cover member downward in a state where the openable and closable lid is open and the second negative pressure in the upper space is released; and the second cover member is made of a material that is configured: (i) not to be plastically deformed by a second suction force from the treatment agent storage space to the waste liquid receipt space in a state where the first negative pressure is generated in the waste liquid receipt space; and (ii) to be broken without being plastically deformed when the depressing force is applied to the first cover member.

2. The waste liquid receptacle according to claim 1, wherein the second cover member is configured to restrict passing of the waste liquid which has been received in the waste liquid receipt space toward the treatment agent storage space.

3. The waste liquid receptacle according to claim 1, wherein:
the second opening has an opening area which is smaller than an opening area of the first opening; and
the first cover member has a press position guide portion which is configured to serve as a mark of a position at which the depressing force is to be applied, the press position guide portion being disposed above the second opening.

4. The waste liquid receptacle according to claim 1, wherein the storage body is configured to protrude toward a waste liquid receipt space side with respect to the upper end of the cylindrical body.

5. The waste liquid receptacle according to claim 1, wherein the housing body is cylindrical.

6. The waste liquid receptacle according to claim 1, wherein the housing body is a flat-bottomed container.

7. The waste liquid receptacle according to claim 1, wherein the first cover member has a laminated structure that includes: a lower layer film joined to the storage body so as to cover the first opening; and an upper layer film adhesively laminated to the lower layer film.

8. The waste liquid receptacle according to claim 7, wherein:
the upper layer film is configured to be peeled off from the lower layer film; and
the lower layer film has a plurality of through holes.

9. A waste liquid reservoir comprising:
a receptacle housing including: a housing body having an upper opening that opens upward; and an openable and closable lid supported by the housing body so as to be capable of opening and closing the upper opening; and
a waste liquid receptacle housed in the receptacle housing and being capable of receiving a waste liquid,
wherein the waste liquid receptacle includes:
a cylindrical body configured to be disposed in the housing body and having an opening on an upper side of the cylindrical body;
a receptacle lid joined to an upper end of the cylindrical body, configured to define an upper space between the receptacle lid and the openable and closable lid on the upper side of the cylindrical body, and defining a waste liquid receipt space for receiving the waste liquid which has been sucked by a first negative pressure generated in the waste liquid receipt space by communicating with the upper space in cooperation with the cylindrical body on a lower side of the upper space; and
a waste liquid treatment agent storage portion disposed on the receptacle lid, the waste liquid treatment agent storage portion being configured to store a waste liquid treatment agent for treating the waste liquid which has been received in the waste liquid receipt space,
wherein the waste liquid treatment agent storage portion includes:
a storage body having a first opening facing the upper space and a second opening facing the waste liquid receipt space, the storage body defining a treatment agent storage space for storing the waste liquid treatment agent between the first opening and the second opening;
a first cover member joined to the storage body so as to cover the first opening; and
a second cover member jointed to the storage body so as to cover the second opening,
wherein:
the first cover member is made of a material that is configured to: (i) be plastically deformed upward by a first suction force from the treatment agent storage space to the upper space in a state where a second negative pressure is generated in the upper space; and (ii) plastically deform downward by a depressing force against the first cover member downward in a state where the openable and closable lid is open and the second negative pressure in the upper space is release; and
the second cover member is made of a material that is configured: (i) not to be plastically deformed by a second suction force from the treatment agent storage space to the waste liquid receipt space in a state where the first negative pressure is generated in the waste liquid receipt space; and (ii) to be broken without being plastically deformed when the depressing force is applied to the first cover member.

10. The waste liquid reservoir according to claim 9, wherein the housing body is cylindrical.

11. The waste liquid reservoir according to claim 9, wherein the housing body is a flat-bottomed container.

12. The waste liquid reservoir according to claim 9, wherein the openable and closable lid includes a press portion configured to restrict upward plastic deformation of the first cover member in the waste liquid receptacle due to the first suction force accompanying the second negative pressure in the upper space becoming equal to or more than a specified value.

13. The waste liquid reservoir according to claim 12, wherein the press portion is configured to be brought into contact with the first cover member when the first cover member is plastically deformed by the first suction force accompanying the second negative pressure in the upper space such that the first cover member reaches a predefined height position.

14. A waste liquid suction system comprising:
the waste liquid reservoir according to claim 7;
a suction source; and
a suction path portion defining a suction path from a suction starting point portion for sucking the waste liquid to the suction source,
wherein:
the waste liquid reservoir is disposed between the suction starting point portion and the suction source on the suction path; and
the waste liquid reservoir is configured to reserve the waste liquid which has been sucked from the suction starting point portion by the suction source.

15. The waste liquid suction system according to claim 14, wherein the housing body is cylindrical.

16. The waste liquid suction system according to claim 14, wherein the housing body is a flat-bottomed container.

\* \* \* \* \*